(12) United States Patent
Berg et al.

(10) Patent No.: US 12,178,695 B2
(45) Date of Patent: *Dec. 31, 2024

(54) DEVICE FOR USE WITH BODY TISSUE SPHINCTERS

(71) Applicant: JT GODFREY, LLC, Hugo, MN (US)

(72) Inventors: James Godfrey Berg, Hugo, MN (US); Thomas Godfrey Berg, Hugo, MN (US)

(73) Assignee: JT GODFREY, LLC, Hugo, MN (US)

( * ) Notice: Subject to any disclaimer, the term of this patent is extended or adjusted under 35 U.S.C. 154(b) by 2 days.

This patent is subject to a terminal disclaimer.

(21) Appl. No.: 18/077,333

(22) Filed: Dec. 8, 2022

(65) Prior Publication Data

US 2023/0099797 A1 Mar. 30, 2023

Related U.S. Application Data

(63) Continuation of application No. 16/857,886, filed on Apr. 24, 2020, now Pat. No. 11,559,385.

(51) Int. Cl.
*A61F 2/04* (2013.01)
(52) U.S. Cl.
CPC .......... *A61F 2/04* (2013.01); *A61F 2002/044* (2013.01)
(58) Field of Classification Search
CPC .................. A61F 2/04; A61F 2002/044; A61F 2210/0014; A61F 2210/0004; A61F 2250/0098; A61B 2017/00827; A61B 17/12013; A61B 2017/00004
See application file for complete search history.

(56) References Cited

U.S. PATENT DOCUMENTS

| 4,271,827 A | 6/1981 | Angelchik |
| 5,006,106 A | 4/1991 | Angelchik |
| 6,146,416 A | 11/2000 | Andersen et al. |

(Continued)

FOREIGN PATENT DOCUMENTS

| CN | 102488571 B | 7/2014 |
| DE | 3011742 A1 | 10/1981 |

(Continued)

OTHER PUBLICATIONS

International Search Report and Written Opinion dated Aug. 2, 2021 for International Application No. PCT/US2021/028654.

*Primary Examiner* — Brian A Dukert
*Assistant Examiner* — Rebecca Lynee Zimmerman
(74) *Attorney, Agent, or Firm* — Seager, Tufte & Wickhem LLP

(57) ABSTRACT

A medical device may include an implantable device for treating a body tissue structure. The implantable device may include a plurality of bodies spaced from adjacent bodies and arranged so as to be configured to extend around an exterior surface of a body tissue structure. The bodies may be configured to apply a static force to the body tissue in a relaxed state and may adjust or move in response to a radially outward force above a threshold level that is acting on one or more of the bodies. The bodies may be pliable and/or made with a pliable material. The bodies may be interconnected via interconnecting regions. One or more of the bodies may be configured to articulate so as to conform to movement of a body tissue structure. A skeletal component may or may not extend through one or more of the plurality of bodies.

17 Claims, 27 Drawing Sheets

(56) References Cited

U.S. PATENT DOCUMENTS

| | | |
|---|---|---|
| 6,432,040 B1 | 8/2002 | Meah |
| 6,764,518 B2 | 7/2004 | Godin |
| 6,773,440 B2 | 8/2004 | Gannoe et al. |
| 7,087,088 B2 | 8/2006 | Berg et al. |
| 7,167,750 B2 | 1/2007 | Knudson et al. |
| 7,220,237 B2 | 5/2007 | Gannoe et al. |
| 7,305,993 B2 | 12/2007 | Tropsha et al. |
| 7,582,110 B2 | 9/2009 | Case et al. |
| 7,662,087 B2 | 2/2010 | Bailly et al. |
| 7,695,427 B2 | 4/2010 | Kugler et al. |
| 7,727,249 B2 | 6/2010 | Rahmani |
| 7,862,502 B2 | 1/2011 | Pool et al. |
| 8,123,768 B2 | 2/2012 | Vardi |
| 8,182,411 B2 | 5/2012 | Dlugos |
| 8,187,164 B2 | 5/2012 | Kugler et al. |
| 8,192,349 B2 | 6/2012 | Schurr et al. |
| 8,282,598 B2 | 10/2012 | Belhe et al. |
| 8,317,677 B2 | 11/2012 | Bertolote et al. |
| 8,357,081 B2 | 1/2013 | Nihalani |
| 8,591,395 B2 | 11/2013 | Ortiz et al. |
| 9,028,394 B2 | 5/2015 | Honaryar et al. |
| 9,211,182 B2 | 12/2015 | Errico et al. |
| 9,526,605 B2 | 12/2016 | Treacy et al. |
| 9,585,783 B2 | 3/2017 | Meade et al. |
| 9,801,747 B2 | 10/2017 | Schwab et al. |
| 9,999,490 B2 | 6/2018 | Rosen et al. |
| 11,033,375 B2 * | 6/2021 | St. Germain ........ A61M 25/003 |
| 2005/0283235 A1 * | 12/2005 | Kugler .................. A61F 5/0069 600/30 |
| 2006/0252983 A1 | 11/2006 | Lembo et al. |
| 2006/0253142 A1 | 11/2006 | Bjerken |
| 2006/0276812 A1 | 12/2006 | Hill et al. |
| 2007/0142699 A1 | 6/2007 | Jandrall |
| 2007/0185374 A1 | 8/2007 | Kick et al. |
| 2008/0097510 A1 * | 4/2008 | Albrecht ............... A61F 5/0003 623/23.65 |
| 2008/0249533 A1 | 10/2008 | Godin |
| 2009/0012542 A1 | 1/2009 | N'diaye et al. |
| 2009/0012546 A1 | 1/2009 | N'diaye et al. |
| 2009/0062825 A1 | 3/2009 | Pool et al. |
| 2009/0240268 A1 | 9/2009 | Kassab et al. |
| 2010/0114327 A1 | 5/2010 | Sobrino-Serrano |
| 2010/0191271 A1 | 7/2010 | Lau et al. |
| 2010/0249901 A1 | 9/2010 | Kang |
| 2010/0280310 A1 | 11/2010 | Raven |
| 2011/0313240 A1 | 12/2011 | Phillips et al. |
| 2012/0083819 A1 | 4/2012 | Wang et al. |
| 2013/0018215 A1 | 1/2013 | Snider et al. |
| 2013/0211189 A1 | 8/2013 | Lau et al. |
| 2013/0211190 A1 | 8/2013 | Fishler et al. |
| 2014/0277573 A1 | 9/2014 | Gill et al. |
| 2015/0164508 A1 | 6/2015 | Hernandez et al. |
| 2016/0158051 A1 | 6/2016 | Mische |
| 2016/0193063 A1 | 7/2016 | St. Germain et al. |
| 2016/0270934 A1 | 9/2016 | Kitano et al. |
| 2017/0112650 A1 | 4/2017 | Hingston et al. |
| 2017/0360550 A1 | 12/2017 | Foote et al. |
| 2019/0029689 A1 | 1/2019 | Shelton, IV et al. |
| 2020/0113720 A1 * | 4/2020 | Jacobs .................. A61F 2/0063 |

FOREIGN PATENT DOCUMENTS

| | | |
|---|---|---|
| WO | 2008117296 A1 | 10/2008 |
| WO | 2015195252 A1 | 12/2015 |
| WO | 2017044929 A1 | 3/2017 |

* cited by examiner

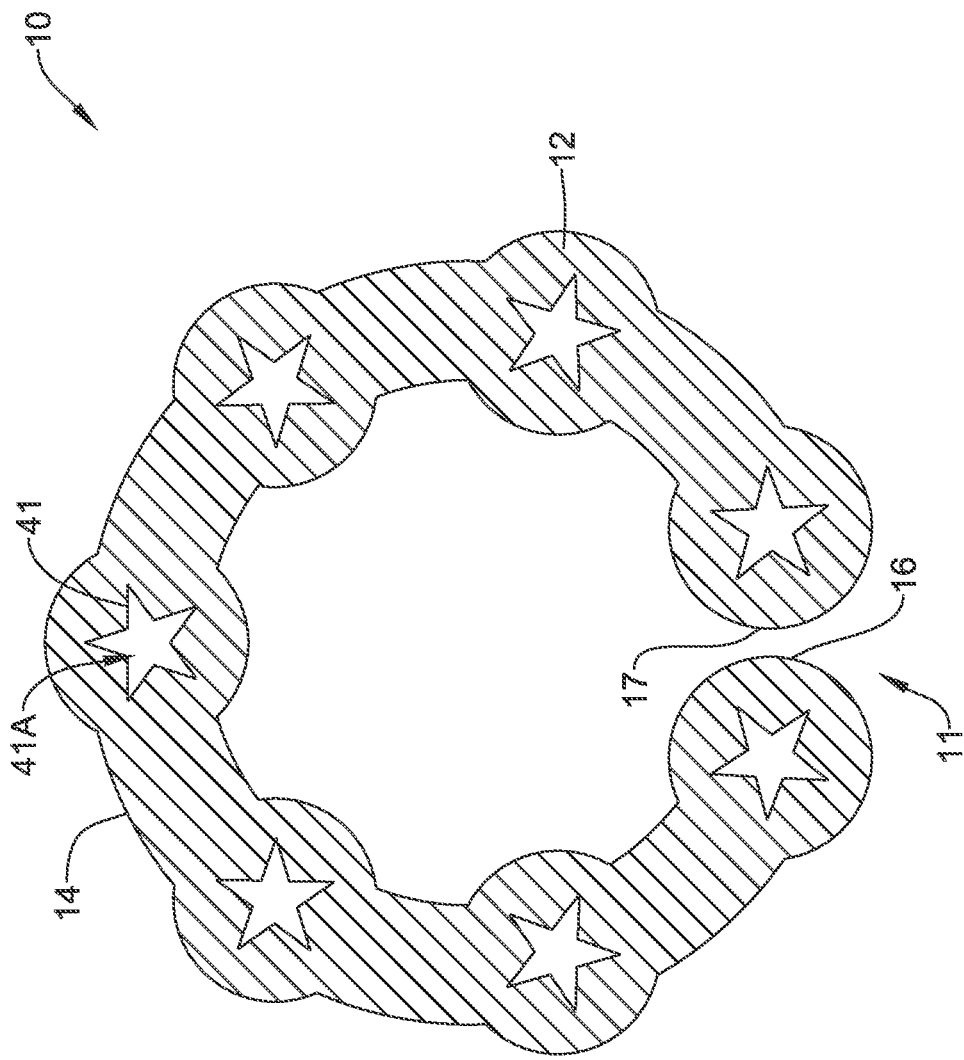

DEVICE FOR USE WITH BODY TISSUE SPHINCTERS

CROSS-REFERENCE TO RELATED APPLICATIONS

This application is a continuation of U.S. patent application Ser. No. 16/857,886, filed Apr. 24, 2020, the entirety of which is incorporated herein by reference.

TECHNICAL FIELD

The present disclosure pertains to medical devices, and methods for manufacturing medical devices. More particularly, the present disclosure pertains to examples of devices for treating body sphincters, and methods for manufacturing and using such devices.

BACKGROUND

Gastro Esophageal Reflux Disease (GERD) may have an effect on the esophagus. A healthy esophagus is a muscular tube that carries food from the mouth into the stomach. A small opening at a distal region of the esophagus leads into the stomach. Muscles in the distal region are known as the lower esophageal sphincter (LES). The LES regulates the passage of food into the stomach, and prevents reflux of acid and food from the stomach back into the esophagus. The LES also regulates the stomach intro-gastric pressures, regulating acidic gasses from refluxing from the stomach back into the esophagus. When properly functioning, the LES will open to allow gasses to be vented from the stomach. A common cause of GERD may include deterioration and/or inadequate functioning of the LES, wherein the LES has lost its ability to resist normal stomach pressure and prevent stomach contents from coming back into the esophagus. This can cause discomfort (e.g., heartburn), and if left untreated, can cause damage to the esophagus that can lead to adverse consequences for the patient.

SUMMARY

This disclosure provides design, material, manufacturing method, and use alternatives for medical devices. An example medical device may include an implantable device for treating a body tissue structure. The implantable device may include a plurality of pliable bodies and an interconnecting region extending between two sequential pliable bodies of the plurality of pliable bodies. Each pliable body may be spaced from an adjacent pliable body of the plurality of pliable bodies. The plurality of pliable bodies and the interconnecting regions may be configured to extend around a body tissue structure such that the plurality of pliable bodies apply a static force to an exterior surface of the body tissue structure in a relaxed configuration and a portion of one or more of the plurality of pliable bodies adjust radially outward in a stressed configuration in response to a radially outward force acting on the one or more of the plurality of bodies.

Alternatively or additionally to any of the embodiments above, the plurality of pliable bodies may have a predetermined height dimension within a range of 3/16" to 1".

Alternatively or additionally to any of the embodiments above, the plurality of pliable bodies may be formed from a silicone material.

Alternatively or additionally to any of the embodiments above, the plurality of pliable bodies and the interconnecting region may connect to form a continuous structure. A closure structure may be configured to connect a first end of the continuous structure to a second end of the continuous structure to form a closed loop.

Alternatively or additionally to any of the embodiments above, the closure structure may include a connector having a first end and a second end, the first end is configured to extend through a first opening extending into a first pliable body of the plurality of pliable bodies and the second end is configured to extend through a second opening extending into a second body of the plurality of bodies.

Alternatively or additionally to any of the embodiments above, the plurality of pliable bodies may be equally spaced apart from adjacent pliable bodies.

Alternatively or additionally to any of the embodiments above, a skeletal component may extend through one or more of the plurality of pliable bodies and the interconnecting region.

Alternatively or additionally to any of the embodiments above, at least one of the plurality of pliable bodies may be configured to articulate independent of articulation of at least one adjacent pliable bodies.

Alternatively or additionally to any of the embodiments above, one or more of the plurality of pliable bodies may include an opening extending at least partially through the pliable body.

Alternatively or additionally to any of the embodiments above, one or more of the plurality of pliable bodies are configured to promote growth of a scar tissue around the implantable device.

Another example implantable device for implantation around a body tissue structure may include a skeletal component which may be configured to form an annular shape in a relaxed state. The implantable device may include a plurality of bodies which may be arranged in a series along the skeletal component. The plurality of bodies may be interconnected forming one continuous structure over the skeletal component and the one continuous structure and the skeletal component are configured to apply a static force to a body tissue when applied to the body tissue and to move radially outward in response to a radially outward force applied to the one continuous structure that is above a threshold level.

Alternatively or additionally to any of the embodiments above, one or more body of the plurality of bodies may be formed from a pliable material.

Alternatively or additionally to any of the embodiments above, the pliable material may be a silicone material.

Alternatively or additionally to any of the embodiments above, two or more bodies of the plurality of bodies may be interconnected with a pliable material.

Alternatively or additionally to any of the embodiments above, the pliable material may encapsulate a first terminal end of the skeletal component and the pliable material may encapsulate a second terminal end of the skeletal component.

Alternatively or additionally to any of the embodiments above, a closure structure may include a first portion located at or adjacent to the first end of the skeletal component and a second portion which may be located at or adjacent to the second end of the skeletal component, wherein the first portion may be configured to releasably engage the second portion to form a closed loop.

Alternatively or additionally to any of the embodiments above, each elongated body of the plurality of elongated bodies may have a predetermined height within a range of 3/16" to 1".

Alternatively or additionally to any of the embodiments above, each elongated body of the plurality of bodies may be configured to articulate about the skeletal component so as to conform to movement of the body tissue.

Alternatively or additionally to any of the embodiments above, the skeletal component may be formed from an elastic material.

Another example implantable device for implantation around a body tissue may include a plurality of bodies which may be formed from a pliable material. Two or more bodies of the plurality of bodies may be interconnected and form a continuous structure which may have a first end and a second end. The plurality of bodies may be configured to move radially outward in response to a radially outward force above a threshold level acting thereon when the plurality of bodies is implanted around a body tissue. One or more bodies of the plurality of bodies may be configured to articulate in response to movement of the body tissue structure.

Alternatively or additionally to any of the embodiments above, the pliable material may be a silicone material.

Alternatively or additionally to any of the embodiments above, one or more pliable body of the plurality of pliable bodies may be configured to promote growth of a scar tissue around the implantable device.

Alternatively or additionally to any of the embodiments above, the implantable device may include a closure structure which may include a first portion located at or adjacent to the first end and a second portion located at or adjacent to the second end, and the first portion may be configured to releasably engage the second portion to form a closed loop.

Alternatively or additionally to any of the embodiments above, the implantable device may include a closure structure which may include a first portion and a second portion, and the first portion of the closure structure may be configured to engage the first end of the continuous structure and the second portion of the closure structure may be configured to engage the second end of the continuous structure to form a closed loop.

Alternatively or additionally to any of the embodiments above, each body of the plurality of bodies may have a predetermined height dimension within a range of 3/16" to 1".

Alternatively or additionally to any of the embodiments above, one or more of the plurality of bodies may include an opening extending into the body.

Alternatively or additionally to any of the embodiments above, the one or more bodies configured to move radially outward in response to the radially outward force above the threshold level acting thereon may include a channel having a wall that is configured to deflect in response to the radially outward force above the threshold level acting on the body.

Alternatively or additionally to any of the embodiments above, one or more of the plurality of bodies may include an opening and an associated channel extending into the body and one or both of the opening and the channel may have a wall configured to deflect in response to the radially outward force above the threshold level acting on the body.

The above summary of some embodiments is not intended to describe each disclosed embodiment or every implementation of the present disclosure. The Figures and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIGS. 23-27 are schematic cross-section views of implantable devices depicting illustrative body configurations.

Figure 1:
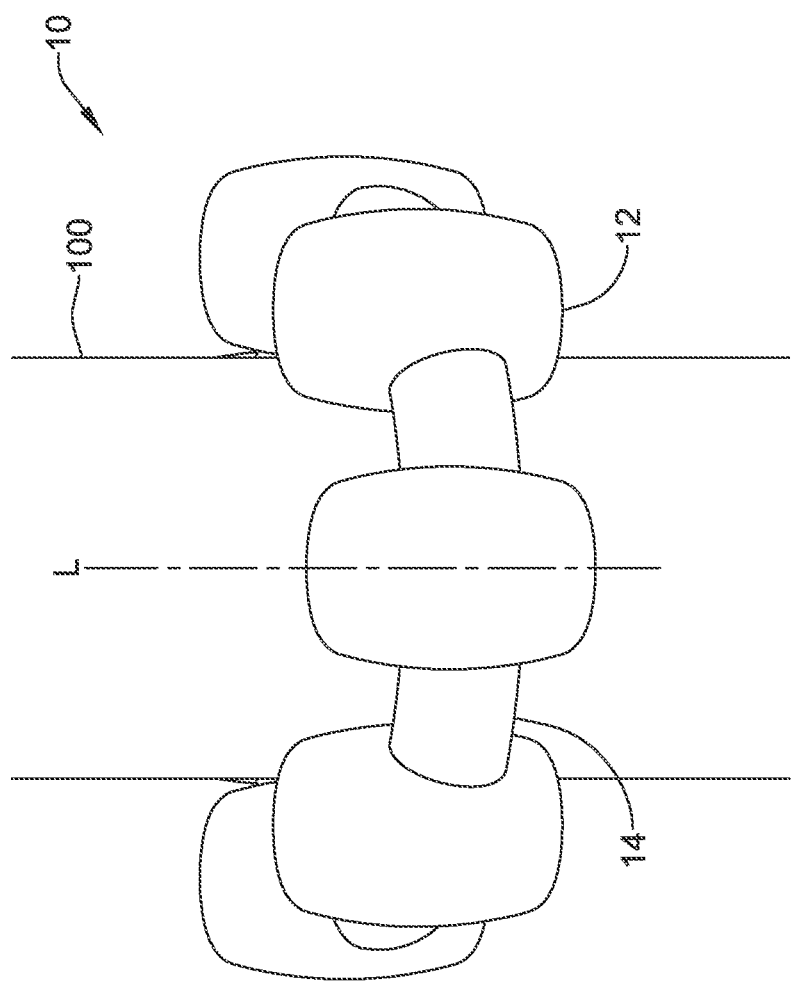
FIG. 1 is a schematic perspective view of an illustrative implantable device shown implanted around a tissue structure in a patient.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit of the disclosure.

DETAILED DESCRIPTION

For the following defined terms, these definitions shall be applied, unless a different definition is given in the claims or elsewhere in this specification.

All numeric values are herein assumed to be modified by the tem "about", whether or not explicitly indicated. The term "about" generally refers to a range of numbers that one of skill in the art would consider equivalent to the recited value (e.g., having the same function or result). In many instances, the term "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

The term "diameter", as used in this specification and the appended claims, is generally employed in its sense as being a line passing from side to side of an object, unless the content clearly dictates otherwise. In some cases, the diameter of an object may pass through a center of the object and/or may be a longest line passing from side to side of the object.

As used in this specification and the appended claims, the singular forms "a", "an", and "the" include plural referents unless the content clearly dictates otherwise. As used in this specification and the appended claims, and although the term "and/or" is sometimes expressly recited herein, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

As discussed above, Gastro Esophageal Reflux Disease (GERD) may include deterioration and/or inadequate functioning of the lower esophageal sphincter (LES), wherein the LES has lost its ability to resist normal stomach pressure and prevent stomach contents from coming back into the esophagus. In some instances, it may be desirable to design an implantable device for implanting around and/or adjacent to a body sphincter (e.g., a body sphincter of a human, a dog, a horse, and/or other suitable animals) that includes sufficient flexibility to be able to conform to a body vessel/lumen and/or tissue around the vessel/lumen and facilitate normal physiological functioning of the body sphincter or similar physiological functioning adjacent the body sphincter (e.g., the implantable device may provide sufficient force at or adjacent to the body sphincter to prevent unintended reflux and/or passage of food, waste, solids, liquids, and/or gasses through a body lumen). In one example device, such as the one discussed in greater detail below, the device may be configured to provide a soft pressure round the body tissue of the vessel/lumen as a result of exerting a radially inward static force on an exterior of the body tissue when in a static state (e.g., a relaxed or substantially relaxed state) and require an internal expansion force (e.g., a force caused an object or fluid in the vessel/lumen trying to pass the body sphincter) above a threshold level to expand beyond a shape of the device in its static state to an expanded shape. In some instances, it may be desirable to design an implantable device for the treatment of GERD which may provide a soft pressure to the LES as well as promote the development of scar tissue around the LES, without leading to erosion of the body tissue. Examples of implantable devices for treating body tissue sphincters with such capabilities and/or other capabilities are disclosed herein.

FIG. 1 illustrates an implantable device 10 shown implanted around a body tissue 100 of a patient, where the implantable device 10 and the body tissue 100 may extend along a longitudinal axis L. As depicted in FIG. 1, the implantable device 10 may include one or more bodies 12 and one or more connector regions 14, but other configurations of the device 10 that may omit the bodies 12 and/or the connector regions 14 and/or include one or more suitable components other than the bodies 12 and connectors regions 14 are contemplated.

The implantable device 10 is an example of a device that may be configured to be positioned around or adjacent to a body tissue structure (e.g., a sphincter) for a variety of medical applications. For example, the implantable device 10 may be used to treat a sphincter in a body (i.e., a human body or an animal body) by facilitating normal physiological functioning of the sphincter thereat and/or similar physiological function adjacent thereto.

The implantable device 10 may be implanted around the body tissue 100 at or adjacent to a sphincter, such as an LES, a pyloric sphincter, a urethral sphincter, an anal sphincter, a rectal sphincter, an ileocecal sphincter, or the like. In one example, the implantable device 10 may be implanted adjacent to or around the LES. In such instances, the implantable device 10 may be configured to apply a static force to the LES, or otherwise act on the LES, in a static state and expand to allow food to pass the LES, while assisting the LES in preventing undesirable reflux from the stomach. The implantable device 10 may be introduced to a patient (e.g., a human and/or other suitable animal) through a laparoscopic, subcutaneous, percutaneous, surgical, and/or one or more other suitable medical procedures, and may be implanted around body tissue of the patient.

Figure 2:
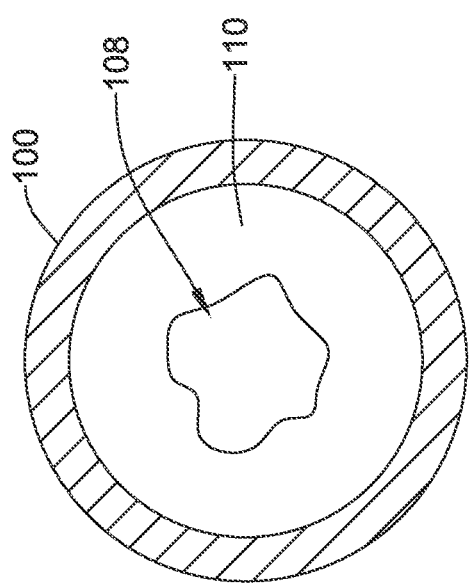
FIG. 2 is a schematic cross-section view of a tissue structure in a patient without an illustrative implantable device implanted.
Figure 3:
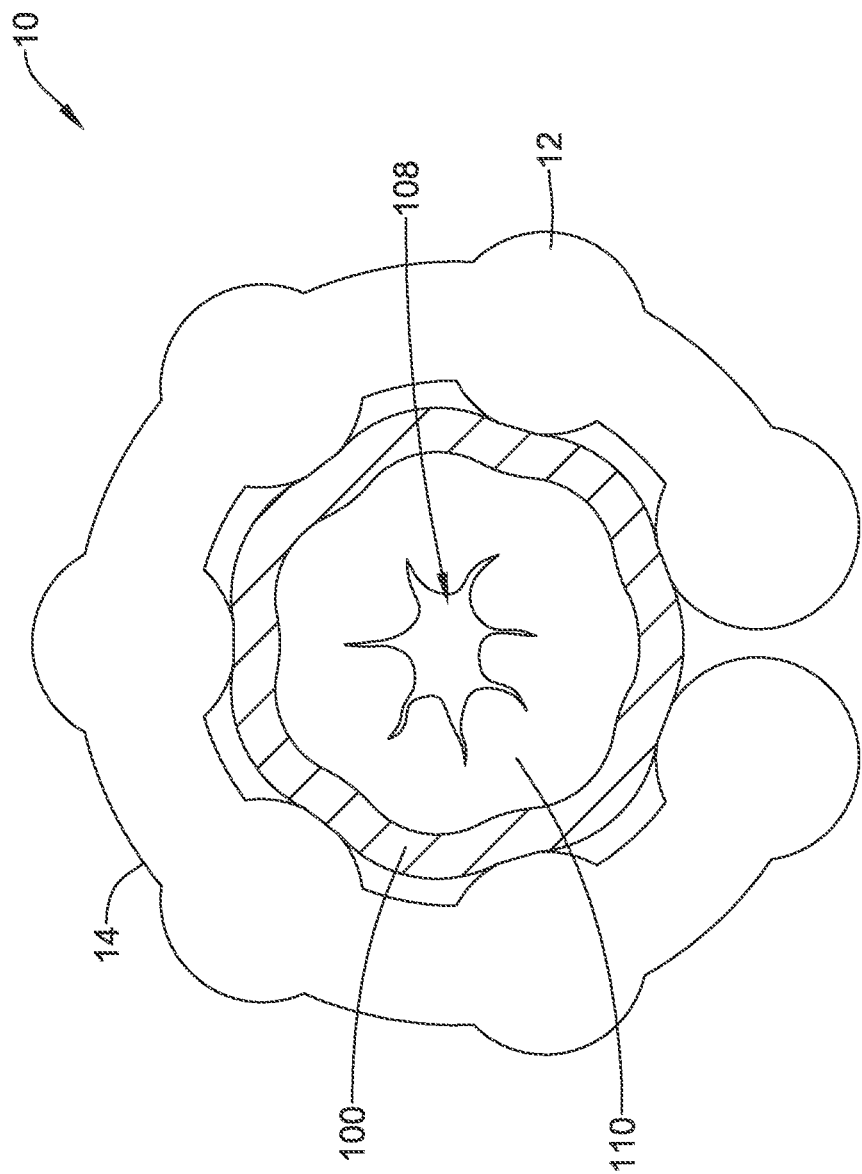
FIG. 3 is a schematic cross-section view of the tissue structure in FIG. 2, with an illustrative implantable device implanted around the tissue structure.

FIGS. 2 and 3 depict cross-section views taken along the body tissue 100 defining a lumen 108, where the cross-section views include an end view of a sphincter 110 (e.g., the LES or other suitable sphincter). As shown in FIG. 2, the sphincter 110 has been damaged and is not able to properly resist passage of objects and/or fluids (e.g., where objects and/or fluids include gasses, solids, and/or liquids) moving through the lumen 108. FIG. 3 depicts the body tissue 100 with the implantable device 10 applied thereto at a position at or adjacent to the sphincter 110, where the implantable device 10 may be applying a soft pressure to the body tissue 100. With the implantable device 10 implanted around or adjacent to the sphincter 110, the sphincter 110 and the implantable device 10 may work together to resist expansion of the lumen 108 until a radially outward expansion force acting on the body tissue 100 from the lumen 108 reaches a threshold level due to a force needed to radially expand the device 10. The threshold level of the radially outward expansion force needed to expand the implantable device 10 (e.g., where the threshold level of the radially outward expansion force may be a function of a spring constant of the implantable device 10) may be set to match a known and desired force needed to open a properly functioning sphincter 110.

Figure 4:
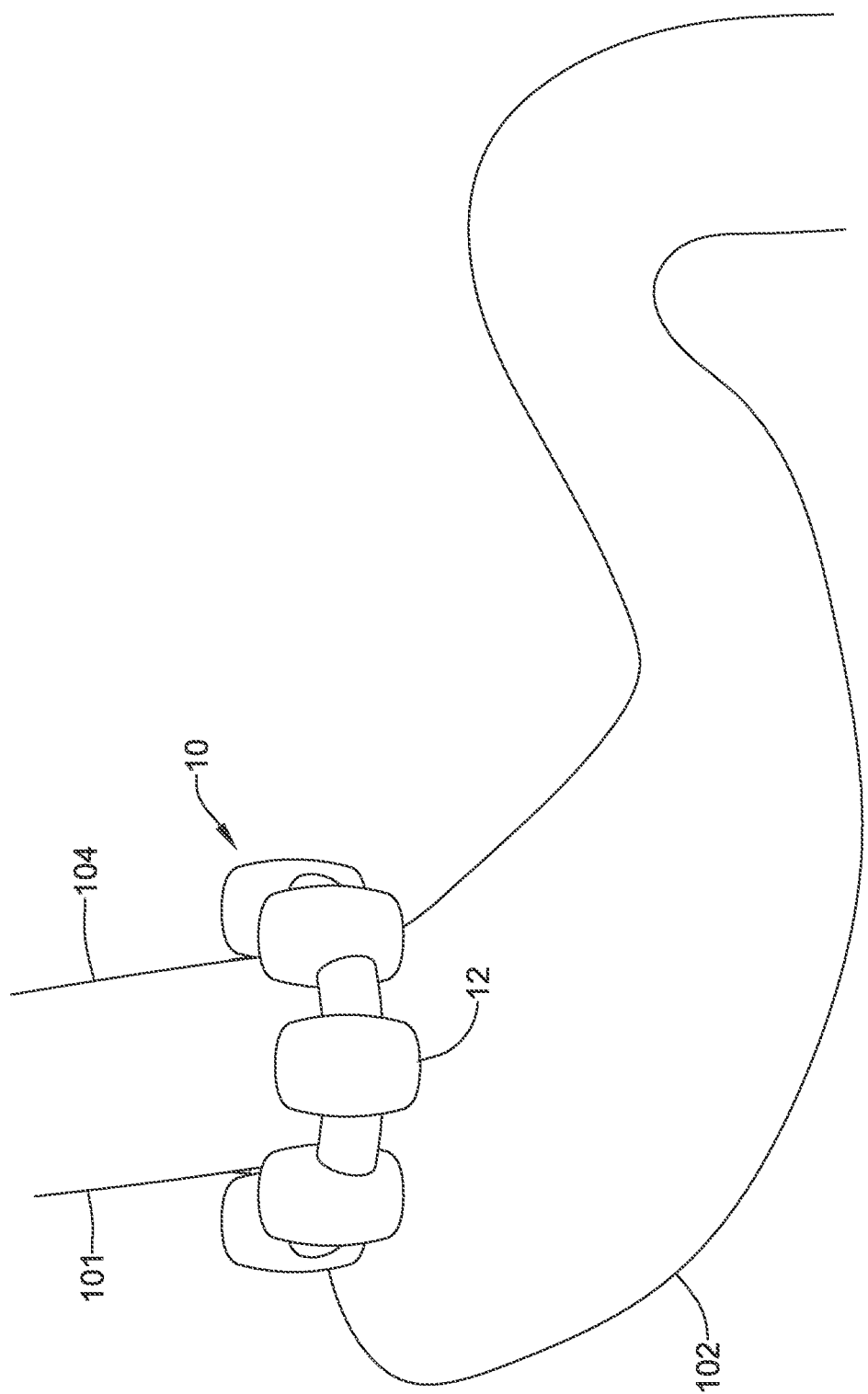
FIG. 4 is a schematic side view an illustrative implantable device shown implanted around a tissue structure in a patient.
Figure 5:
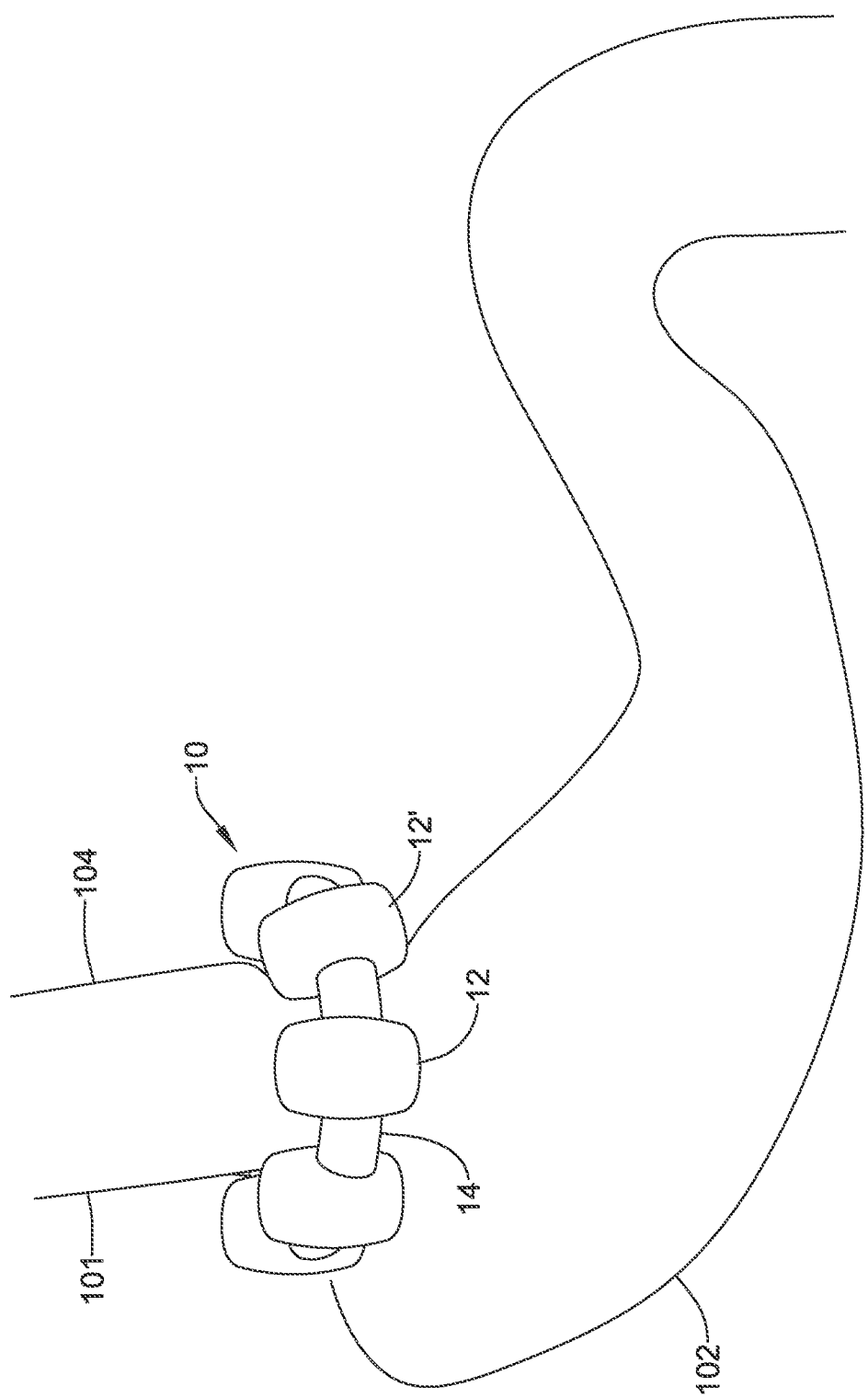
FIG. 5 is a schematic side view of the illustrative implantable device shown implanted around a tissue structure in a patient as depicted in FIG. 4, where features of the illustrative implantable device are adjusted in response to movement of the tissue structure.

FIGS. 4 and 5 illustrate the implantable device 10 shown implanted around or adjacent to a lower esophageal sphincter (LES) 104 (e.g., around a body tissue) providing soft pressure to body tissue of and/or between an esophagus 101 and a stomach 102. The implantable device 10 (e.g., the plurality of bodies 12 and/or other suitable components of the implantable device 10) may be formed to allow, when implanted around the LES 104, passage of food and drink from the esophagus 101 into the stomach 102 and to prevent or limit reflux of food and/or stomach contents back into the esophagus 101 from the stomach 102 that may occur due to gastroesophageal reflux disease (GERD) and/or other diseases or issues. FIG. 4 depicts the implantable device 10 implanted around body tissue, where the implantable device 10 is in its static state. As discussed in greater detail below, one or more of the plurality of bodies 12 of the implantable device 10 may be formed such that the one or more bodies 12 may articulate or flex freely (e.g., relative to one or more other bodies 12 and/or one or more connector regions) to conform to the body tissue as the body tissue moves so as to minimize or mitigate erosion of the body tissue at contact locations between the implantable device 10 and the body tissue while providing adequate forces to the body tissue. FIG. 5 depicts the implantable device 10 implanted around the body tissue, where a body 12' of the bodies 12 is articulated in response to a change in shape of the body tissue (e.g., the change in shape of the body tissue may be in response to an object or fluid within the body tissue).

Figure 6:
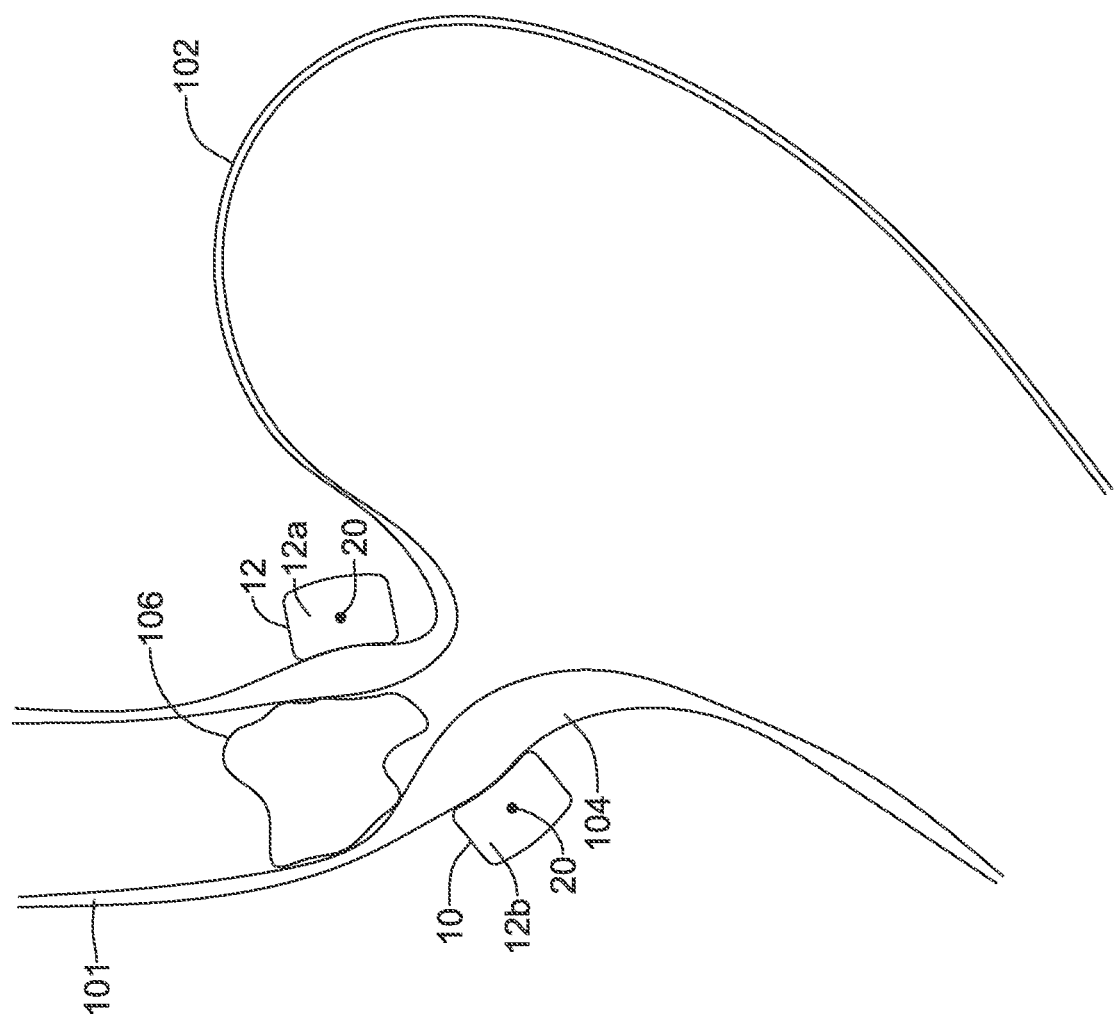
FIG. 6 is a schematic cross-section view of an illustrative implantable device shown implanted around a tissue structure in a patient.

FIG. 6 depicts a cross-section view of the implantable device 10 shown implanted around the LES 104 providing soft pressure to the body tissue of or between the esophagus 101 and the stomach 102. Also shown in FIG. 6, is a bolus 106 (e.g., a bolus 106 of a solid, liquid, and/or gas) traveling through a lumen of the esophagus 101 and engaging the LES 104. When a patient swallows, the bolus 106 travels from the mouth of the patient through the esophagus 101 to the stomach 102 via peristaltic motion and when the bolus 106 reaches the LES 104, a pressure or force from the bolus 106 acts upon the LES and/or or more of the plurality of bodies 12 of the implantable device 10. In response to a radially outward pressure or force from the bolus 106, one or more of the plurality of bodies 12 and/or the implantable device 10 may articulate (e.g., flex, twist, rotate, expand, and/or articulate in one or more other suitable manners) and conform to movement of the esophagus 101 and/or the LES 104 as the esophagus and/or the LES 104 moves in response to forces acting thereon by the bolus 106 and peristaltic motion. For example, as shown in FIG. 6, a first body 12a may deflect (e.g., articulate, flex, twist, and/or move radially outward) in response to the bolus 106 engaging the LES 104, while a second body 12b may not deflect or may deflect differently relative to deflection of the first body 12a. Further, an amount of radially outward force applied from the bolus 106 and the peristaltic motion to the LES 104 and/or the implantable device 10 may reach a threshold level and cause the implantable device 10 to expand to facilitate passage of the bolus 106. Although the threshold level of radially outward force (e.g., which may be equal to or substantially equal to an expansion force needed to expand the implantable device from its static state) may be reached by the act of swallowing, for example, the threshold level of radially outward force may serve to prevent reflux of contents from the stomach 102 back into the esophagus 101. Example threshold levels of radially outward force are discussed in greater detail below.

Figure 7:
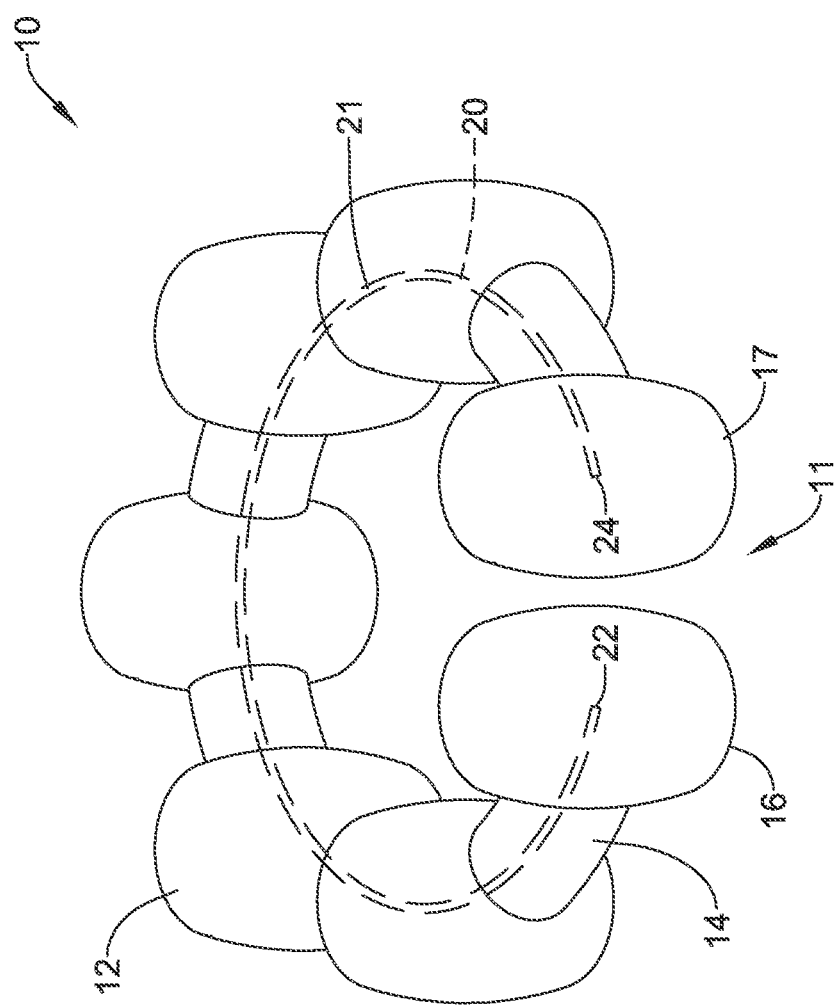
FIG. 7 is a schematic perspective view of an illustrative implantable device.
Figure 8:
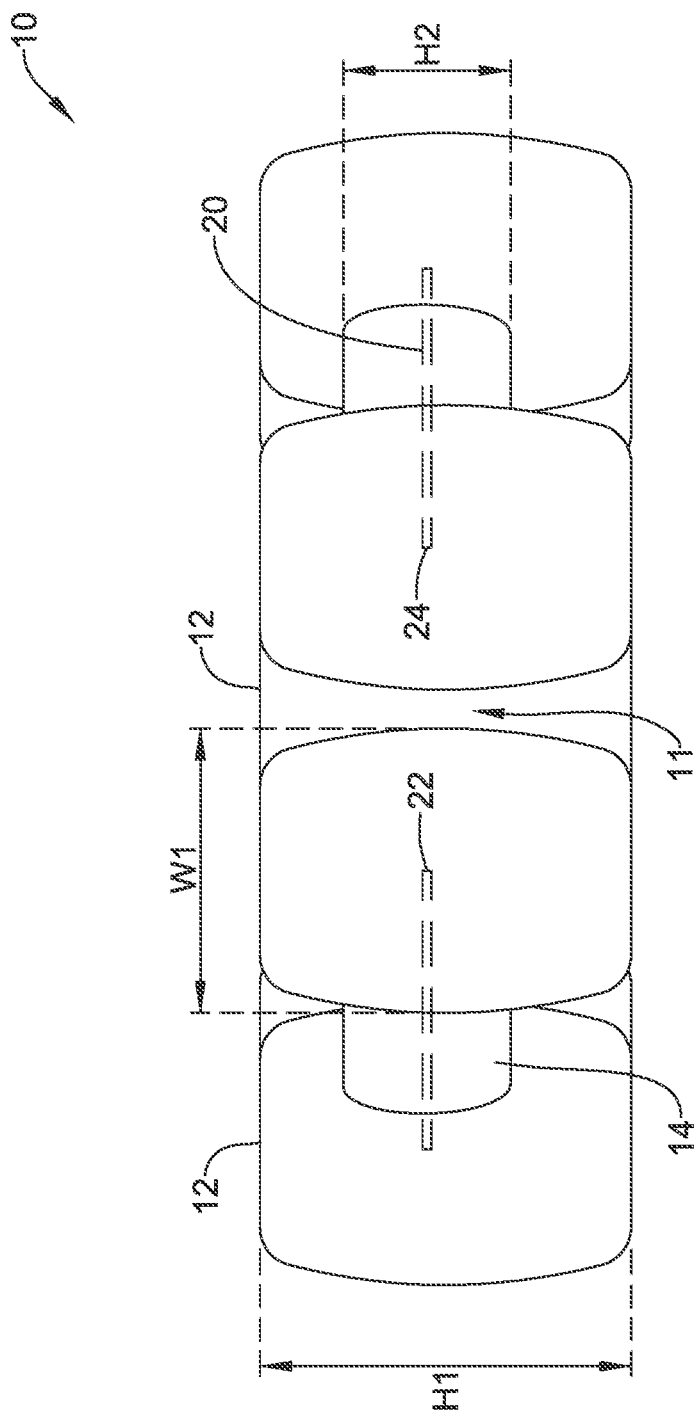
FIG. 8 is a schematic side view of the illustrative implantable device in FIG. 7.

FIG. 7 depicts a perspective view of an illustrative implantable device 10. The implantable device 10 depicted in FIG. 7 may include a skeleton or a skeletal component 20 (e.g., a skeletal framework such as one or more elongated wires or wire structures and/or other suitable skeletal component(s)) which may be formed into a full or partial annular shape when in a relaxed configuration (e.g., when a force external to the implantable device 10 is not acting on the implantable device 10). The skeletal component 20 may be a ring member 21. The ring member 21 may be formed from a single wire or may include a plurality of wires connected to form a ring shape when in a relaxed position and/or one or more other suitable skeletal features. As discussed above, the implantable device 10 may include a plurality of bodies 12, which may be arranged in series such that each adjacent one of the plurality of bodies 12 may be positioned at a predetermined distance, as shown in FIG. 8 (e.g., a predetermined shortest distance in a relaxed state of the implantable device 10) from an adjacent one of the plurality of bodies 12 (note, not all bodies are labeled for clarity purposes). The skeletal component 20 may be configured to extend through each one of the plurality of bodies 12 such that the plurality of bodies 12 and the skeletal component 20 may form an annular-shaped implantable device 10.

As discussed, the implantable device 10 may be designed to be positioned around or adjacent to a body tissue structure (e.g., a sphincter, such as the LES, by positioning the implantable device 10 at or around body tissue of the esophagus or other suitable body tissue) to provide a soft, conformable compression force (e.g., the static force) to the body tissue structure, as discussed with respect to FIGS. 1-6. When implanted around body tissue, the skeletal component 20 and/or other materials of the implantable device 10 may require a sufficient amount of radially outward force to be applied to the body tissue structure adjacent to the implantable device 10 before the implantable device 10 and/or an adjacent sphincter expands, which may serve to prevent reflux from the stomach into the esophagus. However, the radially outward force needed to expand the implantable device 10 and/or an opening of the adjacent sphincter may not be so great as to prevent opening of the sphincter during swallowing or venting of excessive pressure from the stomach. After the swallowing or stomach venting event, compression force provided by the skeletal component 20 and/or other components of the implantable device 10 may assist the sphincter in closing to prevent reflux.

In some instances, properties of the material used to form the skeletal component 20, a number of wire segments and/or other suitable skeletal features used to form the skeletal component 20, dimensions (e.g., a thickness, shape, diameter, etc.) of the wire(s) and/or skeletal features used to form the skeletal component 20, and/or materials of other components used to form the implantable device 10 may contribute to a threshold level of force needed to expand the implantable device from its relaxed state and/or, when implanted, from its static state. A threshold level of force needed to expand the implantable device 10 may be determined and/or configured based on the body tissue to which the implantable device 10 is to be applied and designed to treat, among other possible factors.

In some cases, components of the implantable device 10 may be formed from a metal (e.g., nickel-titanium alloys, such as nitinol, and/or one or more other suitable metals), a polymeric material (e.g., silicone, polyetheretherketone (PEEK), polyethylene terephthalate (PET), and/or one or more other suitable polymers), a microporous material (e.g., a microporous foam and/or one or more other suitable microporous materials), a foam material (e.g., a closed cell foam material, an open cell foam material, and/or one or more other suitable foam materials), other suitable materials and/or a combination of metallic materials, polymeric material, microporous materials, foam materials, and/or other suitable materials. One example of a polymeric, microporous material may be a silicone foam. Additionally, one or more portions of, or an entirety of, the implantable device 10 may include a bioabsorbable and/or biodegradable material (e.g., bioabsorbable and/or biodegradable metals, polymers, and/or other materials including, but not limited to silk, silicon, plastic, magnesium, etc.) In one example of the implantable device 10, the skeletal component 20 may be formed, at least in part, from an elastic material (e.g., nitinol, elastic polymer (e.g., silicone materials and/or other suitable elastic polymers), and/or other suitable materials having elastic properties). When elastic materials are used to form the skeletal component 20 of the implantable device 10 and/or other portions of the implantable device 10 (e.g., the pliable bodies 12, the interconnecting regions 14, and/or other suitable portions of the implantable device 10), the skeletal component 20 and/or other portions of the implantable device 10 may impart a pressure or force (e.g., a radially inward static pressure or force) around the body tissue to which the implantable device 10 is applied and may result in changing the movement of the sphincter (e.g., changing an ability of the sphincter to expand) in response to solids, liquids, and/or gasses passing through a lumen defined by the body tissue such that the body tissue moves and/or functions similar to a properly functioning adjacent body sphincter.

The implantable device 10 the plurality of bodies 12 may be configured to be positioned around the skeletal component 20. In some instances, the plurality of bodies 12 may be positioned around an entirety of the skeletal component 20 (e.g., 360 degrees about the skeletal component 20). However, this is not required.

The implantable device 10 may include any suitable number of bodies 12. In one example, as shown in FIG. 7, the implantable device 10 may include seven (7) bodies 12. It is contemplated that the implantable device 10 may include one or more other suitable number of bodies 12 (e.g., one, two, three, six, ten, twelve, etc.) A number of bodies 12 included in the implantable device 10 and a location of those bodies 12 may be selected such that desired forces applied by the implantable device 10 to the body tissue structure in response to radially outward forces acting on the body tissue structure are at desired locations.

In some examples (e.g., as depicted in FIG. 7), the plurality of bodies 12 may be interconnected. For example, the plurality of bodies 12 may be interconnected by a plurality of connector regions 14 (note, not all connector regions 14 are labeled for clarity purposes), where a connector region 14 may be positioned between adjacent bodies 12 of the plurality of bodies 12.

One or more of the interconnected bodies 12 and/or other suitable bodies 12 may be configured to articulate or flex relative to a resting position and/or relative to one or more other body 12 (e.g., the body 12 may articulate or flex independently of one or more other bodies 12). In some cases, material forming the interconnector regions 14 may be configured to facilitate absorbing twisting motion of the body 12 such that the body 12 may articulate or flex independently of adjacent bodies 12. One example material that may facilitate independent articulation or flexing of the bodies 12 may be a silicone material (e.g., a silicone foam material), but other materials, including those materials discussed herein, may be utilized. In some cases, one or more of the plurality of bodies 12 may not be interconnected (e.g., one or more of the connector regions 14 may be omitted), as shown, for example, in FIGS. 19 and 20.

The plurality of bodies 12 and the plurality of connector regions 14, may be configured to form one continuous structure, however, this is not required and the plurality of bodies 12 and the plurality of connector regions 14 may be configured to form two or more continuous or interconnected structures. In some cases, the bodies 12 and the connector regions 14 may be formed as separate components relative to the skeletal component 20, such that the plurality of bodies 12 and the connector regions 14 may be independently articulated, flexed, and/or twisted relative to the skeletal component 20 (e.g., the bodies 12 and/or the connector regions 14 may not be fixed to the skeletal component 20 so as to prevent or limit articulation, twisting, or flexing of the bodies 12 and/or the connector regions 14). In this manner, the plurality of bodies 12 may be configured such that they may articulate or flex freely about (e.g., independent from) the skeletal component 20 so as to conform to the body tissue around which the implantable device 10 is implanted. As discussed in greater detail below, when the implantable device 10 may be formed without an internal skeleton or skeletal component 20, the bodies 12 may still be configured to articulate or flex with respect to one another and/or the connector regions 14.

The skeletal component 20 of the implantable device 10 may include a first end 22 and a second end 24, and as discussed above, the skeletal component 20 may be configured to extend through one or more of the plurality of bodies 12 such that the plurality of bodies 12 and the skeletal component 20 form an annular implantable device 10. The first end 22 of the skeletal component 20 and the second end 24 of the skeletal component 20 may be separate from one another (e.g., as shown in FIGS. 7-10). The implantable device 10 having separated ends may result in the implantable device 10 forming an annular c-shape in a relaxed state with an opening 11 between bodies 12 adjacent the first end 22 and the second end 24 of the skeletal component 20, which may allow the implantable device 10 be elongated when implanting the implantable device 10 in a patient.

The plurality of bodies 12 and/or the interconnecting regions 14 of the implantable device 10 may be configured to provide a contact surface with the body tissue that may mitigate or prevent erosion of the body tissue. In one example, the plurality of bodies 12, the interconnecting regions 14, and/or other suitable portions of the implantable device 10 may be formed from a pliable material (e.g., a foam, a microporous material, and/or a polymeric material such as, but not limited to, silicone, PEEK, PET, and/or one or more other suitable polymers). The pliable material may provide a flexibility that may allow pressure relief and/or conformation of the implantable device 10 to the body tissue.

In some cases, it may be desirable to facilitate preventing migration of the implantable device 10 by promoting growth of scar tissue around the implantable device 10. In addition to anchoring the implantable device 10 in place, the progressive growth of scar tissue over time may thicken the body tissue to which the implantable device 10 is applied and may improve performance of the implantable device 10 by allowing the body tissue to slowly adjust to the presence of the implantable device 10, and further help control the normal functions of the body tissue structure (e.g. LES). In some cases, scar tissue growth may be encouraged at some or all locations at which the implantable device 10 contacts the body tissue.

When the implantable device 10 is formed from a bioabsorbable and/or biodegradable material, the implantable device 10 may be configured to form scar tissue along the body tissue such that once the bioabsorbable and/or biodegradable material absorbs and/or degrades, the remaining scar tissue facilitates operation of a sphincter in a manner similar to as when the implantable device 10 was located around the body tissue, as discussed herein. For example, the scar tissue remaining after the implantable device 10 has absorbed and/or degraded may cause the body tissue to be more or less expandable, flexible, and/or pliable based on locations of the scar tissue, which may facilitate control of flow through a lumen defined by the body tissue without leaving a long term implant around the body tissue.

Although not shown, in some examples, the implantable device 10 may include a coating encapsulating part(s) of or an entirety of the implantable device 10. In some instances, the implantable device 10 may include one or more layers (i.e., one or more coverings, coatings, etc.) of material positioned on and/or adjacent to the material forming the plurality of bodies 12, the skeletal component 20, and/or the connector regions 14 that are configured to promote growth of scar tissue. The coating may be configured to promote tissue growth at one or more locations and/or prevent tissue growth at one or more locations along the implantable device 10.

FIG. 8 is a schematic side view of the illustrative implantable device 10 depicted in FIG. 7. As shown in FIG. 8, the plurality of bodies 12 may have a predetermined height H1 and/or width W1 (e.g., a diameter when the body 12 has a cylindrical shape) so as to provide a desired contact surface with the body tissue. In some cases, the desired contact surface area with the body tissue may be configured to facilitate applying soft pressure or static force from the implantable device 10 to the body tissue by providing a surface area that is configured to prevent or reduce pressure points between the implantable device 10 and the body tissue and mitigate chances of developing necrosis of the body tissue due to the forces applied thereto by the implantable device 10.

Example dimensions of the plurality of bodies 12 include any suitable height H1 and/or width W1. Example heights H1 of the bodies 12 include, but are not limited to, a height H1 may be a value of or between about 3/16 of an inch to about one (1) inch, about ¼ inch to about ¾ inches, or other suitable range. In some cases, the height H1 of a body 12 may be about 3/16 inch, about ¼ inch, about ½ inch, about ¾ inch, about one (1) inch, and/or other suitable size. Example widths W1 of the bodies 12 include, but are not limited to, a width W1 may be a value of or between about 3/16 inch to about ½ inch or other suitable range. In some cases, the width W1 of a body 12 may be about 3/16 inch, about ¼ inch, about ½ inch, and/or other suitable size. Further, although all of the bodies 12 and the connecting regions 14 of the implantable device 10 are depicted in the FIGS. as having similar or same dimensions as other bodies 12 and connecting regions 14, respectively, one or more body 12 and/or one or more connecting region 14, may have one or more dimensions different than one or more dimension of other bodies 12 and/or interconnecting regions 14, respectively.

The height H1 and the width W1 may be suitable to create a desired surface area (e.g., a large surface area relative to existing devices), such that the implantable device 10 provides a soft pressure to the body tissue. The height H1 and width W1 dimension of the implantable device 10 may be configured to prevent or reduce pressure points between the implantable device 10 and the body tissue structure and mitigate the chances of developing necrosis of the body tissue structure due to the forces applied thereto by the implantable device 10. For example, the surface area provided by the height H1 and the width W1 of the plurality of bodies 12 may be configured to reduce the amount of pressure applied to the body tissue by increasing the surface area of the plurality of bodies 12, thereby reducing the pressure (e.g., a function of $p=F/A$, where p is pressure applied by the body 12, F is a radially inward force applied by the body 12, and A is a surface area of the body 12 configured to contact body tissue) applied at contact points between the bodies 12 and the body tissue.

Further, the dimensions of the plurality of bodies 12 may be designed to promote growth of scar tissue around the implantable device 10, and over time, the implantable device 10 may become overgrown with scar tissue. For example, as shown in FIG. 8, the plurality of bodies 12 may include a larger height H1 and/or width W1 (e.g., a larger surface area) that may be configured to create a desired contact surface for promoting increased growth of scar tissue, as opposed to expected scar tissue that results from a smaller height and/or width (e.g., a smaller surface area) of the plurality of bodies 12.

As shown in FIG. 8, the plurality of connector regions 14 may have a height H2. In some examples, the height H2 of the plurality of connector regions 14 may be less than the height H1, may be equal to the height H1, and/or may have varying heights along the connector regions 14. The height H2 of the plurality of connector regions 14, together with the skeletal component 20 when included, may contribute to establishing a threshold force level needed to expand the implantable device 10 from its static state around body tissue. The height H2 of the plurality of connector regions 14 may further aid in increasing the surface area of the implantable device 10 that is contacting body tissue, thereby reducing the pressure on the body tissue.

Figure 9:
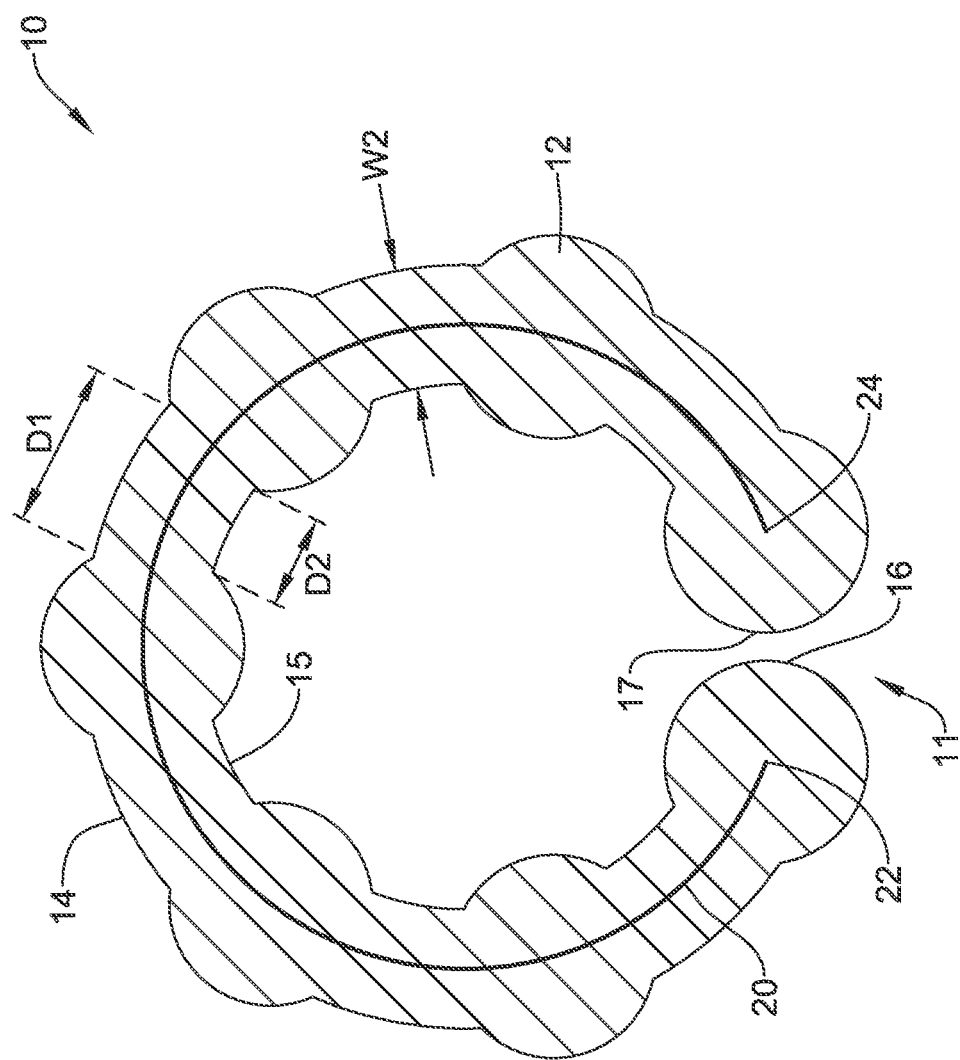
FIG. 9 is a schematic cross-section view of an illustrative implantable device.
Figure 10:
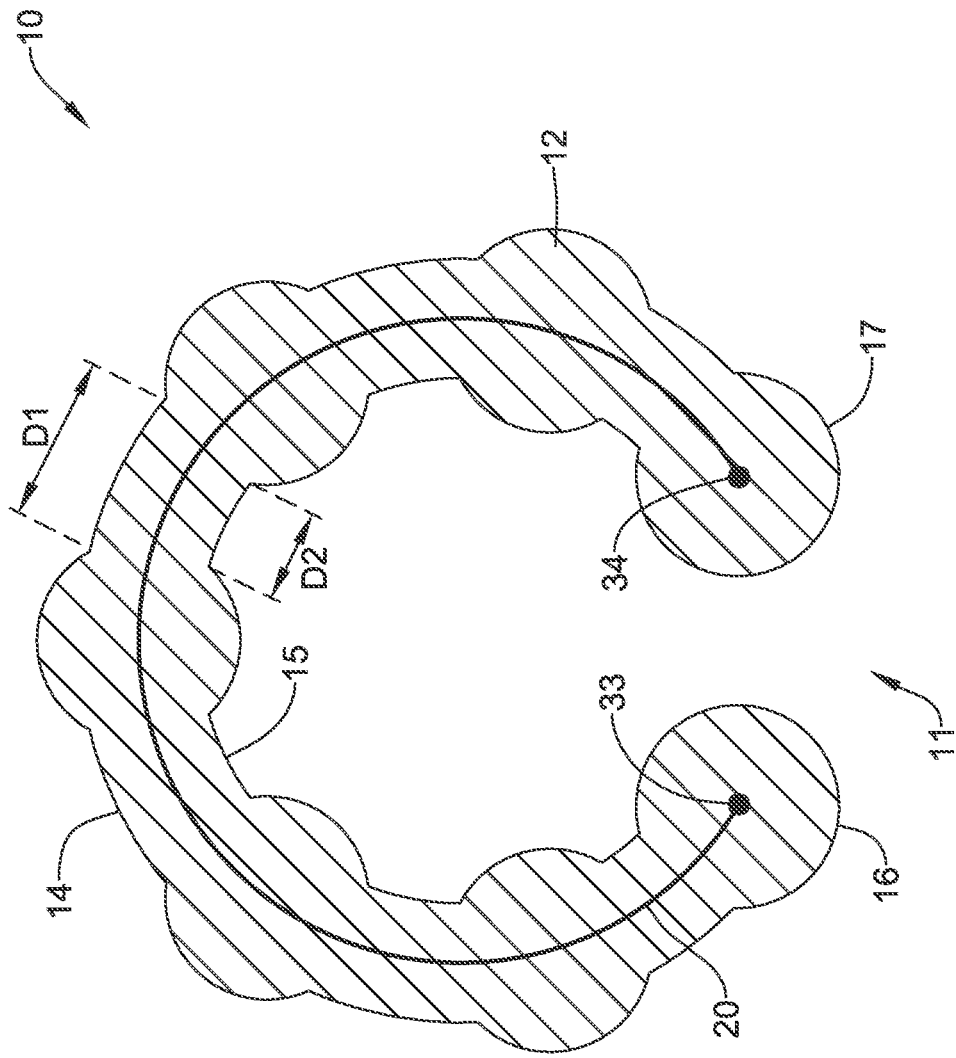
FIG. 10 is a schematic cross-section view of an illustrative implantable device.
Figure 11:
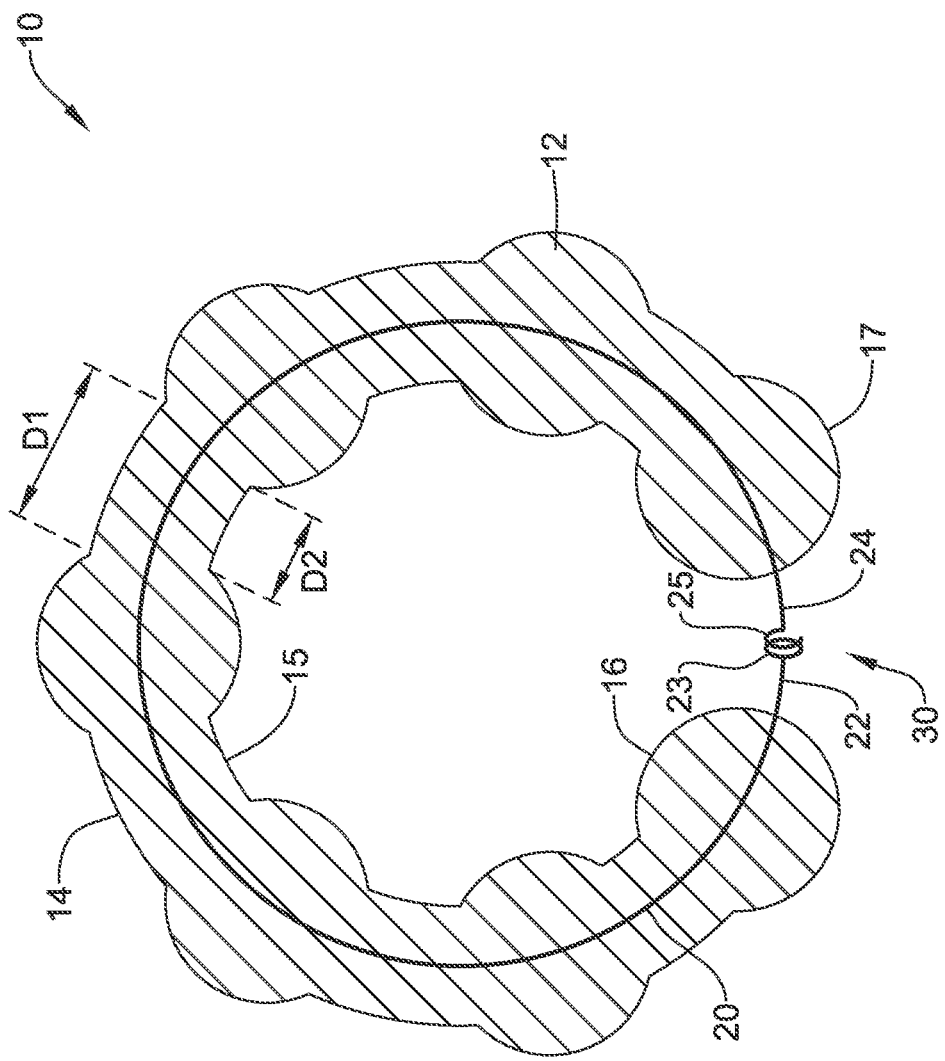
FIG. 11 is a schematic cross-section view of an illustrative implantable device.

FIGS. 9-11 are cross-section views of the illustrative implantable device 10. FIGS. 9-11 depict various end-structures of the implantable device 10, as discussed below. Further, as shown in FIGS. 9-11, the connector regions 14 may include a first distance D1 and a second distance D2 between each adjacent body 12, along with a width W2. In some examples, the first distance D1 may be the same as the second distance D2 and/or the first distance D1 may be different than the second distance D2. The first distance D1 and/or the second distance D2 may be a predetermined distance (e.g., as measured when the implantable device 10 is in a relaxed state) from an adjacent one of the plurality of bodies 12. In one example, the first distance D1 may be a value of or between about 0.030 inches to about 0.375 inches and the second distance D2 may be a value of or between about 0.020 inches to about 0.250 inches. The width W2 of the connector regions 14 may be any suitable value. In one example, the width W2 of the connector regions 14 may be a value of or between about 0.060 inches to about 0.250 inches. Other suitable values for D1, D2, and W2 are contemplated.

As shown in FIG. 9, the implantable device 10 may be designed in an annular C-clamp or similar configuration where the ends 22 and 24 of the skeletal component 20 are not connected (e.g., are separated by the opening 11) and the rigidity of the skeletal component 20 and material of the bodies 12 and the connector regions 14, in combination with an annular shape of the skeletal component 20, may facilitate maintaining the implantable device 10 around a body structure when implanted there around. In some instances, as shown in FIG. 7, the ends 22, 24 of the skeletal component 20 may not extend beyond a first terminal end 16 of the implantable device 10 (e.g., adjacent material forming the bodies 12 and/or connector regions 14) and a second terminal end 17 of the implantable device 10 (e.g., adjacent material forming the bodies 12 and/or the connector regions 14). When the ends 22, 24 of the skeletal component 20 do not extend beyond the terminal ends 16, 17, the terminal ends 16, 17 may form atraumatic terminal ends 16, 17 to prevent undesirable puncturing of tissue. In some cases, the atraumatic ends may be formed by bodies 12 or other suitable components of the implantable device 10. In some instances, when the implantable device 10 may be implanted around the lower esophageal sphincter, the opening 11 between first and second ends 22, 24 of the skeletal component 20 and terminal ends 16, 17 of the implantable device 10 may be designed such that the opening 11 fits around a vagus nerve or other suitable body feature.

The skeletal component 20 may include various features to prevent undesirable puncturing of the material forming the bodies 12 and/or puncturing of the body tissue. In some cases, the ends 22, 24 of the skeletal component 20 may include atraumatic, rounded, and/or ball-shaped features. In one example, as shown in FIG. 10, the skeletal component 20 may be formed with a first atraumatic feature 33 and a second atraumatic feature 34 that each may include a ball structure attached to or formed from the material forming the skeletal component 20. It may be contemplated that other suitable atraumatic features may be included in the ends 22, 24 of the skeletal component 20.

As shown in FIG. 11, the implantable device 10 may include a closure structure 30. The closure structure 30 depicted in FIG. 11 may be formed from or attached to the skeletal component 20 and may be adjacent to the first end 22 of the skeletal component 20 and the second end 24 of the skeletal component 20 for facilitating forming the implantable device 10 into a closed loop having an open interior. Although the closure structure 30 may take-on one or more various forms for connecting ends of the skeletal component 20 and/or ends of the implantable device 10, the closure structure 30 depicted in FIG. 11 may include a first portion 23 (e.g., a loop) and a second portion 25 (e.g., a hook). Examples of additional or alternative closure structures include, but are not limited to, a mechanical latch, a magnetic connector, a tubular closure, a suture, a clasp, or the like. In some instances, the closure structure 30 may be omitted (e.g., as shown in FIGS. 7-10).

In some instances, when the implantable device 10 may be implanted around the lower esophageal sphincter, the closure structure 30 may be designed such that the closure structure 30 fits around the vagus nerve without contacting the vagus nerve. By including a closure structure 30 that fits around the vagus nerve, dissection of the vagus nerve is not required. In some instances, the closure structure 30 is not required.

Figure 12:
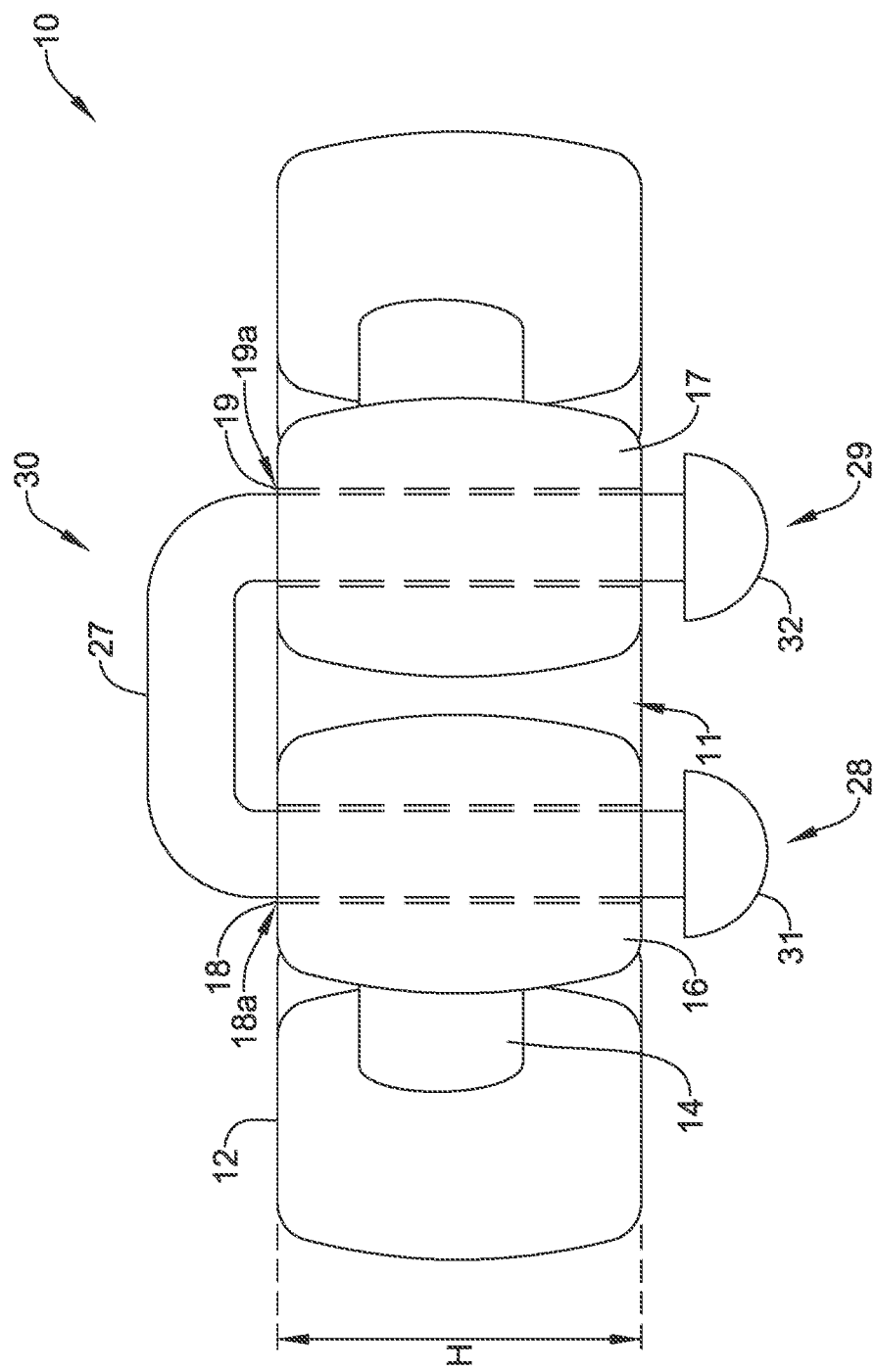
FIG. 12 is a schematic front side view of an illustrative implantable device depicting an illustrative closure structure.

FIG. 12 depicts an example implantable device 10 with a closure structure 30 that may include a connector 27 extending through the first terminal end 16 and the second terminal 17 of the implantable device 10. In some examples, as shown in FIG. 12, the first terminal end 16 may include a first opening 18, and the second terminal 17 end may include a second opening 19. The first opening 18 may be configured to extend through a center of or other suitable portion of the first terminal end 16, and the second opening 19 may be configured to extend through a center of or other suitable portion of the second terminal end 17, thereby effectively forming a first channel 18a, and a second channel 19a, respectively, as indicated by the dashed lines in FIG. 12. The connector 27 may extend through the first opening 18, the second opening 19, the first channel 18a, and the second channel 19a to secure the terminal ends 16, 17 of the implantable device 10 relative to one another.

In some examples, each body 12 of the plurality of bodies 12 may include an opening and/or a channel (e.g., first channel 18a, second channel 19a) extending entirely or partially therethrough. In other examples, one or more of the plurality of bodies 12 and/or the first terminal end 16 and/or the second terminal end 17 may not include a channel. These are just examples. When included, the openings and/or channels may provide greater flexibility to the plurality of bodies 12, which may contribute to the soft pressure provided by the implantable device 10 and absorption of radial outward forces acting on the implantable device 10.

The connector 27 may be configured from any suitable material configured to flex and/or bend in response to radially outward forces acting thereon and/or on the implantable device 10. The connector 27 may be made from any suitable materials including, but not limited to, silicone, foams, PEEK, PET, nitinol, stainless steel, etc., and/or combinations thereof.

The connector 27 may be formed using any suitable manufacturing technique. Example manufacturing techniques suitable for forming the connector 27 included, but are not limited to, molding techniques, additive techniques (three-dimensional printing, etc.), subtraction techniques (e.g., etching, lathing, etc.), stretching techniques, and/or other suitable manufacturing techniques.

As shown in FIG. 12, the connector 27 may have a first end 28 and a second end 29. The connector 27 may be configured to extend through the first opening 18 of the first terminal end 16 and the second opening 19 of the second terminal end 17. In some cases, the first end 28 of the connector 27 may include a first retaining member 31. In this manner, when the first end 28 extends through the first opening 18, the first retaining member 31 serves to provide a stop such that the first end 28 may not be pulled back through the first opening 18. Similarly, the second end 29 of the connector 27 may include a second retaining member 32. When the second end 29 extends through the second opening 19, the second retaining member 32 serves to provide a stop such that the second end 29 may not be pulled back through the second opening 19, thereby securing the first terminal end 16 to the second terminal end 17.

To facilitate insertion of the first retaining member 31 through the first opening 18 and the second retaining member 32 through the second opening 19, the first retaining member 31 and/or the second retaining member 32 may configured from a pliable material. Alternatively or additionally, the material of the bodies 12 forming the first opening 18 and/or the second opening 19 may be formed from a pliable material to facilitate receiving the first and second retaining members 31, 32. Further, in some cases, the first retaining member 31 and/or the second retaining member 32 have a rounded (as shown in FIG. 12) and/or beveled side to facilitate one-way insertion into the openings 18, 19 and the channels 18a, 19a.

Although not shown, in some examples, the closure structure 30 may include a suture. The suture may include a loop formed by tying a knot between, or otherwise coupling (e.g., heat bonding, adhesive, etc.) a first end and a second end of the suture. The first end may be configured to extend through the first opening 18 of the first terminal end 16 and the second end may be configured to extend through the second opening 19 of the second terminal end 17. The first end and the second end may then be tied in a knot and/or connected in one or more other suitable manners, thereby forming a closed suture loop.

Figure 13:
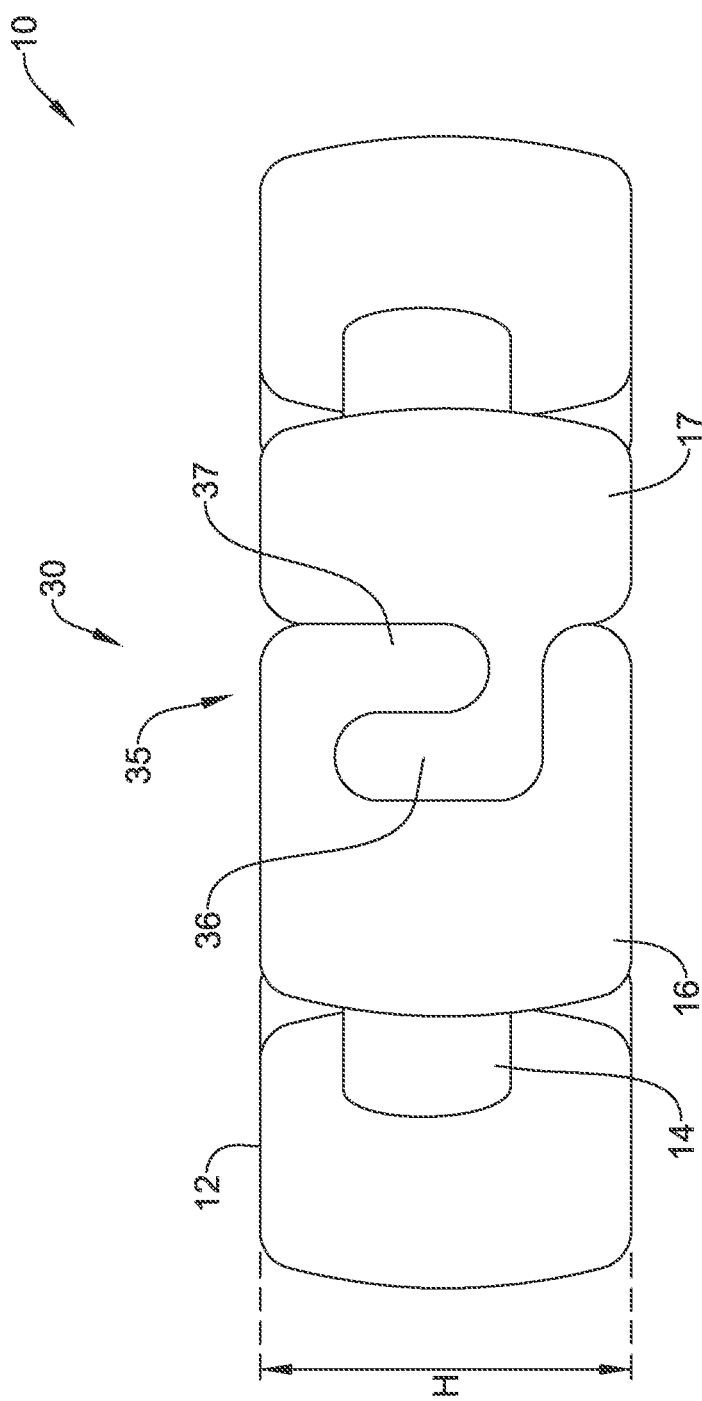
FIG. 13 is a schematic front side view of an illustrative implantable device depicting an illustrative closure structure.

FIG. 13 depicts another example closure structure 30, wherein the closure structure 30 includes a clasp 35. In some cases, the clasp 35 may be formed from the material used to form the bodies 12, but this is not required. Additionally or alternatively, the clasp 35 may be formed from components connected to the skeletal component 20 and/or to the material forming the bodies 12 and/or the connector regions 14. In one example, the clasp 35 may include a first clasp element 36 formed using material of the first terminal end 16 and a second clasp element 37 formed using material of the second terminal end 17. The first clasp element 36 may be configured to engage with the second clasp element 37 in a dovetail fashion, as depicted in FIG. 13, or other suitable manner, thereby securing the first terminal end 16 to the second terminal end 17 of the implantable device 10. Other suitable clasp 35 materials and/or configurations are contemplated.

When the closure structure 30 is utilized, radially outward force acting on the implantable device 10 may act different on the implantable device 10 than when no closure structure 30 is utilized. For example, when the closure structure 30 is utilized, the ends of the implantable device 10 cannot separate and as a result, the radially outward force acting on the implantable device 10 acts differently when the ends of the implantable device 10 are connected than when the ends of the implantable device 10 are not connected to one another.

Figure 14:
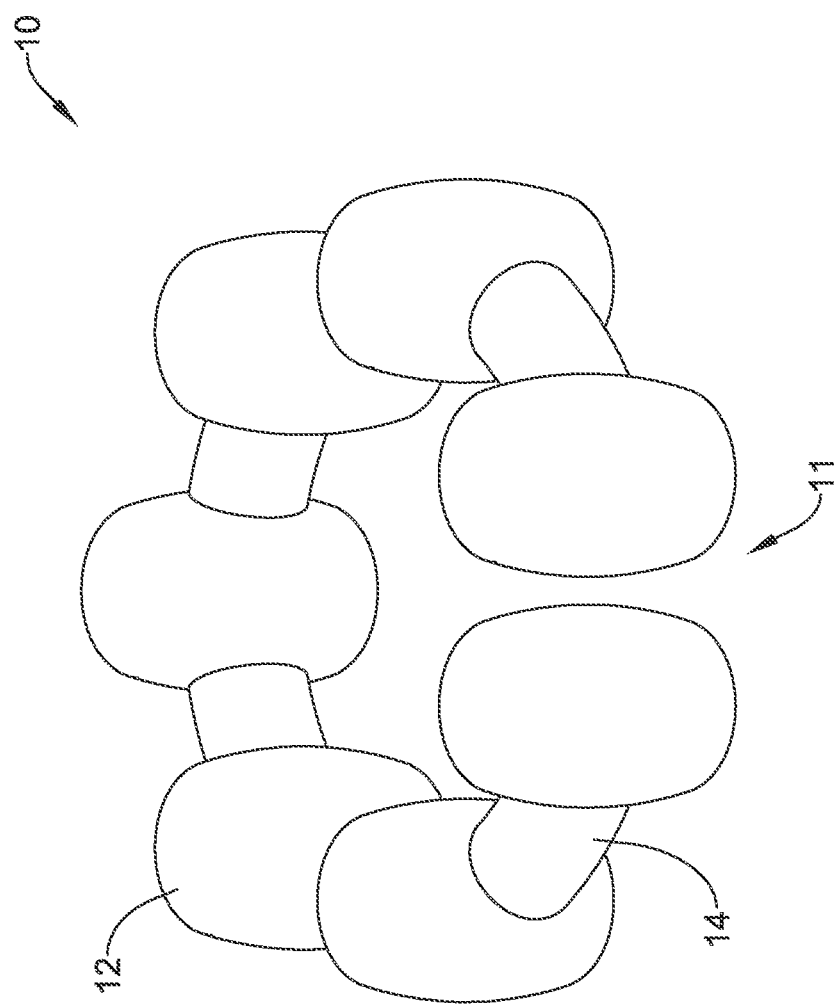
FIG. 14 is a schematic perspective view of an illustrative implantable device.
Figure 15:
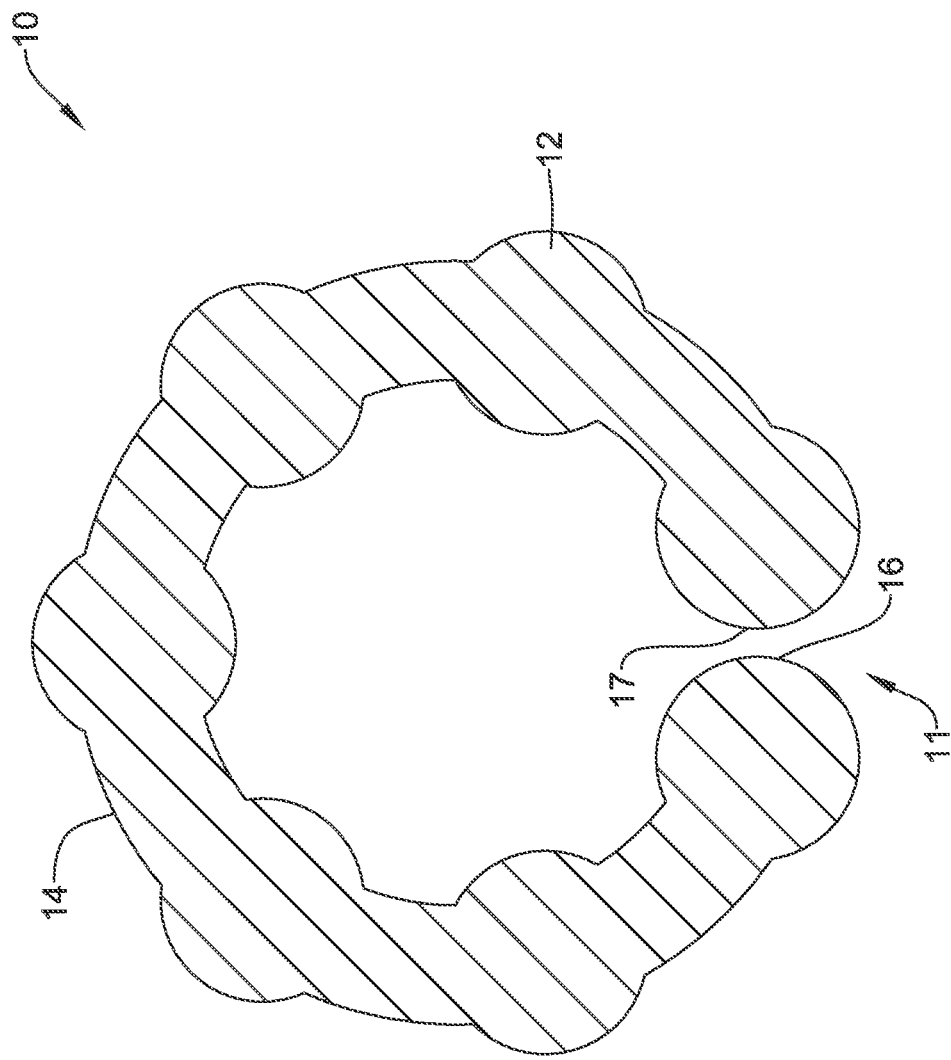
FIG. 15 is a schematic cross-section view of the illustrative implantable device depicted in FIG. 11.

FIGS. 14 and 15 depict an illustrative implantable device 10 in a perspective view and a cross-section view, respectively, which may include the plurality of bodies 12 and the connector regions 14. The implantable device 10 may differ from the implantable device 10 depicted in FIG. 1, however, in that the implantable device 10 of FIG. 14 may be configured without a skeletal component (e.g., the skeletal component 20) or other skeleton component extending through the bodies 12, as depicted in the cross-section view of FIG. 15. In some cases, two or more of the plurality of bodies 12 may be interconnected by connector regions 14 positioned between adjacent bodies of the plurality of bodies 12. The bodies 12 and the connector regions 14 of the implantable device 10 that omits the skeletal component 20 may be configured to require a threshold amount of force to radially expand when implanted body tissue so as to facilitate or simulate proper operation of a sphincter adjacent an implant site similar to forces the provided by the configuration of the implantable device 10 that includes the skeletal component 20.

When the skeletal component is included and/or when the skeletal component is omitted, properties of the material (e.g., Shore A values, density, elasticity, firmness, etc.) used to form the implantable device 10 and/or dimensions (e.g., a thickness, shape, etc.) of the plurality of bodies 12 and/or the connector regions 14 used to form the implantable device 10 may contribute to the rigidity of the implantable device 10. As a result, material properties and dimensions of the bodies 12 and/or connector regions 14 may be adjusted to provide a desired static force for the implantable device 10 as applied to the body tissue and/or to set a radially outward threshold force value that may need to be overcome to expand the implantable device 10 (e.g., cause one or more bodies 12 and/or other portions of the implantable device 10 move radially outward from a static force position).

In some cases, the implantable device 10 that does not include the skeletal component 20 or other skeleton component, may have components formed from or may include a material the same as or similar to the material used for the bodies 12 and/or the connector regions of the implantable device 10 including the skeletal component 20, discussed above. In one example, silicone may be used to entirely or at least partially form the bodies 12 and the connector regions 14 of the implantable device 10. In some cases, the material(s) used to form the implantable device 10 that does not include the skeletal component 20 or other skeleton component may have a Shore A value of or between about Shore one (1) A and about Shore seventy (70) A.

In some cases, the material(s) and the dimensions of the implantable device 10 omitting the skeletal component 20 and/or other skeleton component may be configured such that a threshold amount of force may be required to expand the implantable device 10. In some instances, the materials and/or dimensions of the implantable device 10 may be configured such that the threshold amount of force is a value of or between about ten (10) grams and about eighty (80) grams, about twenty (20) grams and about eighty (80) grams, about thirty (30) grams and about seventy (70) grams, about thirty-five (35) grams and about forty-five (45) grams, about thirty-eight (38) and forty-two (42 grams, and/or within one or more other suitable ranges. In one example, the threshold amount of force required to expand the implantable device 10 may be set at or about forty (40) grams.

Figure 16:
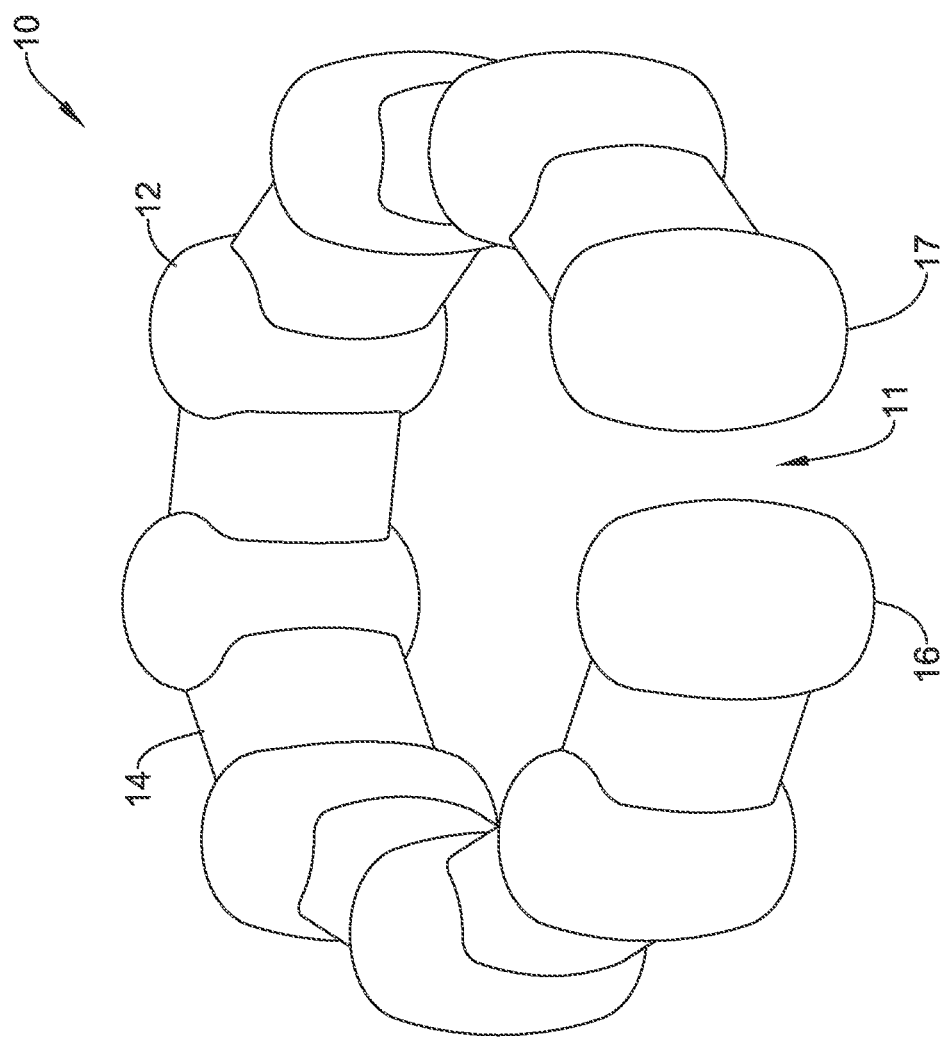
FIG. 16 is a schematic perspective view of an illustrative implantable device.

FIG. 16 depicts an illustrative implantable device 10 in a perspective view, which may include the plurality of bodies 12 interconnected by the connector regions 14 positioned between adjacent bodies 12 of the plurality of bodies 12. The implantable device 10 depicted in FIG. 16 may be similar to the implantable device 10 in FIG. 14, but may differ from the implantable device 10 depicted in FIG. 14 in that the connector regions 14 may have a greater height than the connector regions 14 in FIG. 14 (e.g., H2 as depicted in FIG. 8). Such differences in height of the connector regions 14 may facilitate configuring the implantable device 10 to require a desired amount force to be applied thereto prior to the implantable device expanding. In some cases, when the connector regions 14 include a greater height relative to heights of other connector regions 14, the implantable device 10 may require a greater radially outward force to expand the implantable device 10 when it is implanted around a tissue body than when the connector regions 14 have a lesser height. In some cases, the implantable device 10 of FIG. 16 may include a skeletal component (e.g., the skeletal component 20) extending through the bodies 12, although this is not required.

Figure 17:
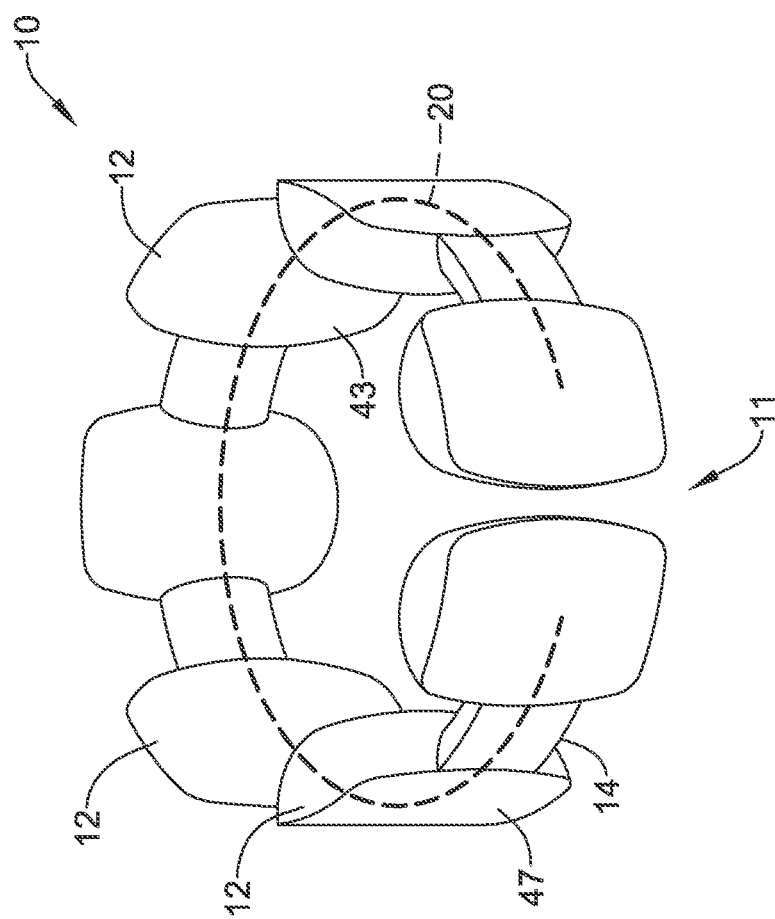
FIG. 17 is schematic perspective view of an illustrative implantable device.
Figure 18:
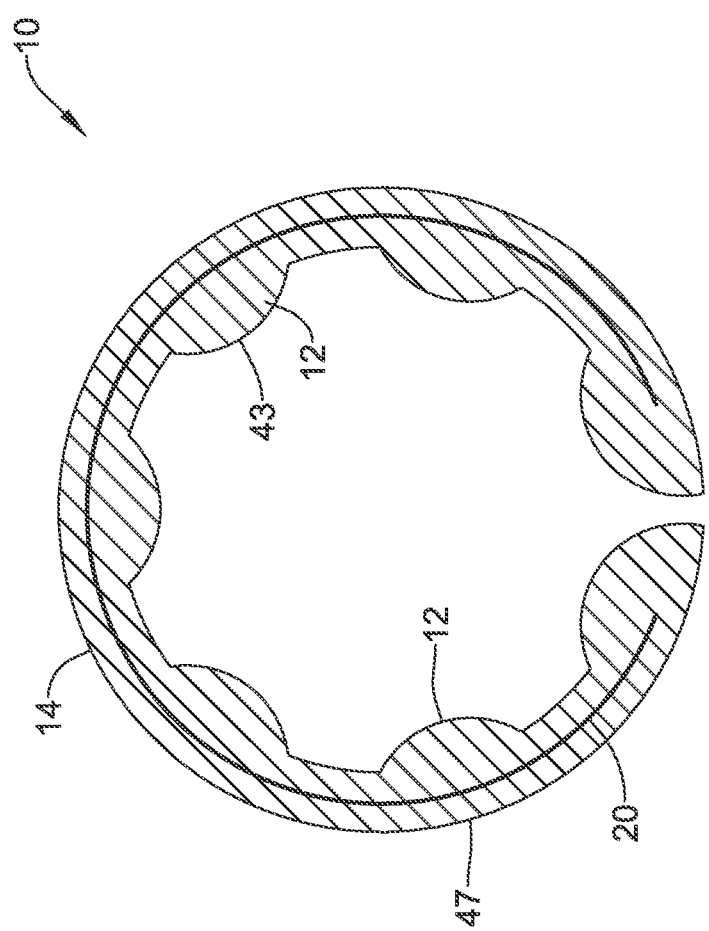
FIG. 18 is a schematic cross-section view of the illustrative implantable device depicted in FIG. 17.

FIGS. 17 and 18 depict an illustrative implantable device 10 in a perspective view and a cross-section view, respectively, which may include a skeletal component 20 and a plurality of bodies 12 distributed about the skeletal component 20 in a manner similar to the configuration depicted in FIG. 7. The bodies 12 of the implantable device 10 configuration depicted in FIGS. 17 and 18, however, may be configured to have a limited or slim profile relative to a profile of the configuration of bodies 12 depicted in FIG. 7. In the example configuration of FIGS. 17 and 18, one or more of the bodies 12 may include an interior region 43 (e.g., a region facing a body tissue when the implantable device 10 has been implanted around the body tissue) having a relatively similar configuration to an interior region configuration of the bodies 12 depicted in FIG. 7, and an exterior region 47 (e.g., a region facing away from a body tissue when the implantable device 10 has been implanted around the body tissue) having a slimmer, less intrusive profile relative to an exterior region configuration of the bodies 12 depicted in FIG. 7 or the interior region 43 configuration of the bodies 12 depicted in FIGS. 17 and 18. In some cases, the bodies 12 having a slim or minimal profile may form an asymmetrical shape about the skeletal component 20 from the interior region 43 to the exterior region 47, as depicted in FIG. 18, but this is not required and the bodies 12 may have a slim or minimal profile that is symmetrical about the skeletal component 20 from the interior region 43 to the exterior region 47. The bodies 12 depicted in FIGS. 17 and 18 may be molded, machined, and/or formed in one or more other suitable manners to have a desired profile, such as a slim or minimal profile that facilitates a desired distribution of forces from the implantable device 10 against body tissue around which the implantable device 10 has been implanted to facilitate operation of a sphincter adjacent the implant location and prevent undesired erosion of the body tissue (e.g., penetration of the implantable device 10 into the body tissue).

The bodies 12 having a slimmer or minimal profile may have any suitable dimension or configuration. In one example, a depth of one or more of the bodies 12 (e.g., a distance from an inner circumference or side of the body 12 to an outer circumference or side of the body 12) having a slimmer or minimal profile, may be a value of or between about 0.060 inches to about 0.250 inches. Other depth dimensions are contemplated.

Figure 19:
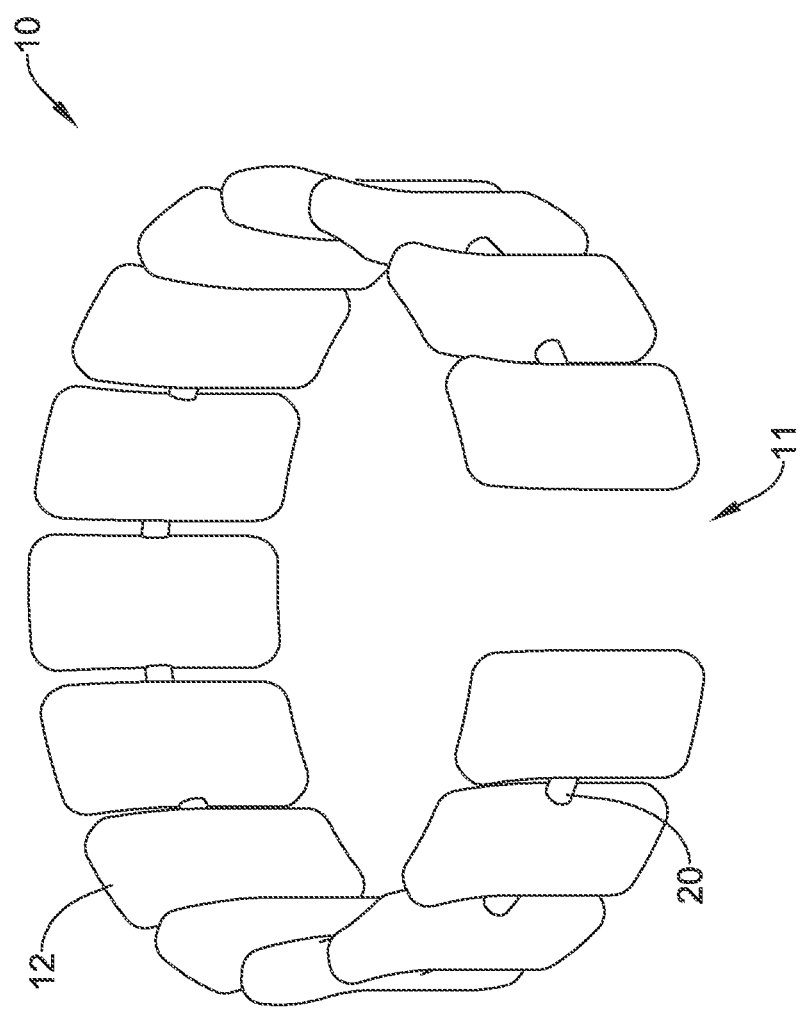
FIG. 19 is a schematic perspective view of an illustrative implantable device.
Figure 20:
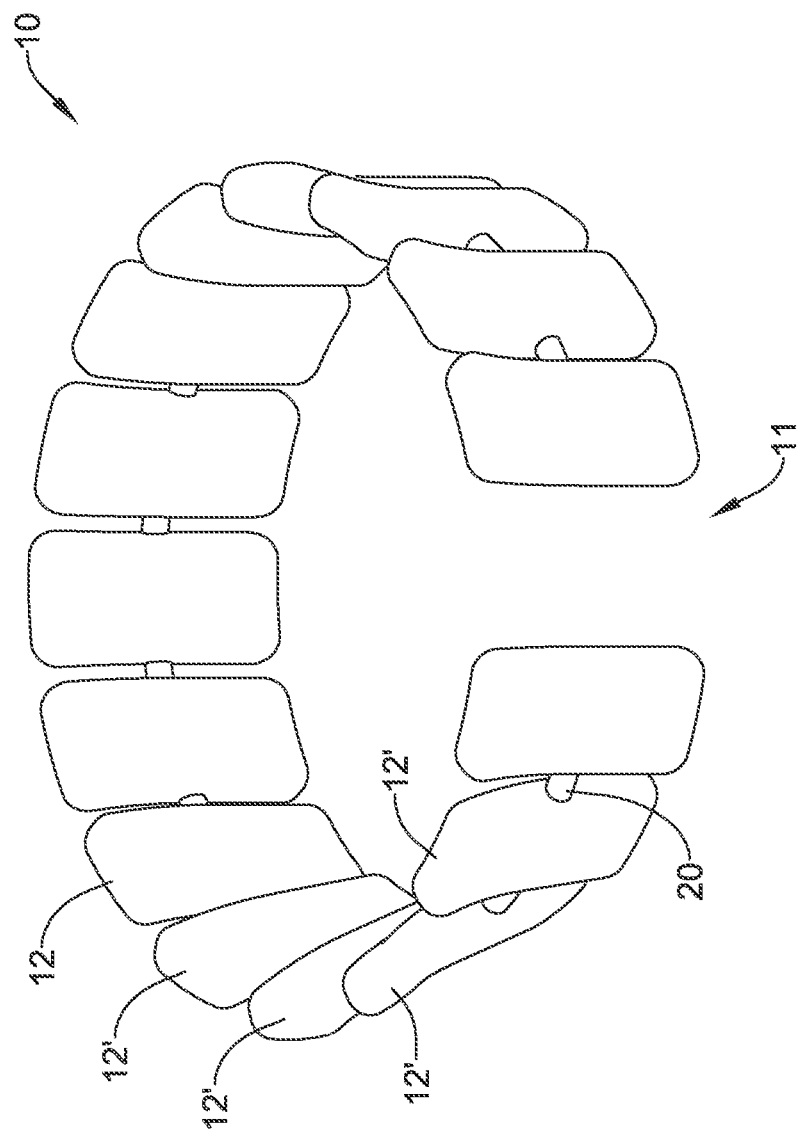
FIG. 20 is a schematic perspective view of an illustrative implantable device.

FIGS. 19 and 20 depict illustrative configurations of the implantable device 10, wherein the plurality of bodies 12 may not be interconnected other than through engagement with the skeletal component 20. FIG. 19 depicts the bodies 12 of the implantable device in a relaxed state. FIG. 20 depicts bodies 12' in various positions articulating about the skeletal component 20.

When the plurality of bodies 12 are not interconnected via connector regions 14, the plurality of bodies 12 may be formed over the skeletal component 20 such that the plurality of bodies 12 may be fixed to the skeletal component 20, held in place by one or more connectors, held in place by one or more stops located on the skeletal component 20 adjacent to a radial edge of the bodies 12, and/or secured about the skeletal component 20 in one or more other suitable manners. The plurality of bodies 12 may be formed from a pliable material so as to conform to the body tissue structure. In some cases, one or more bodies 12' of the plurality of bodies 12 may be configured to articulate or flex about the skeletal component 20, as depicted in FIG. 20.

As shown in FIGS. 19 and 20, the bodies 12 may have a three-dimensional rectangular shape. A surface area of the bodies 12 having such a configuration may be configured to facilitate a greater contact area between the bodies 12 and body tissue, relative to an amount of contact area between the bodies 12 and the body tissue when using a rounded or barrel-type body 12, depicted with respect to other FIGS. herein. Further, to facilitate initiating articulation or flexing of the bodies 12 and/or other movement of the bodies 12 in response to movement of body tissue, the bodies 12 may be and/or may have an arched section, where ends of the a body 12 may be arched radially outward, but this is not required.

FIGS. 21-27 depict schematic views of illustrative implantable devices 10 having openings 41 (e.g., openings that may be similar to or different from the openings 18, 19, discussed above) and associated channels 41a (e.g., channels similar to or different from the channels 18a, 19a, discussed above) extending at least partially through (e.g., part of the way through or entirely through) one or more bodies 12. Note, for clarity purposes, not all openings 41 and channels 41a are marked with reference numerals.

Although the openings 41 and the associated channels 41a are depicted as extending all of the way through the implantable device 10 in the views of FIGS. 21-27, it is contemplated that the openings 41 and the channels 41a may extend only partially through one or more of the bodies 12. Further, although the configurations of the implantable device 10 depicted in FIGS. 21-27 do not include the skeletal component 20 extending through the implantable device 10 as a skeleton in the manner discussed above, it is contemplated the openings 41 and/or the associated channels 41a with one or more of the shapes disclosed herein and/or other suitable shapes may be utilized when the skeletal component 20 is included in the implantable device 10. That is, configurations of the implantable device 10 with or without the skeletal component 20 may include the openings 41 and/or the associated channels 41a.

In some cases, the openings 41 and/or the channels 41a may be configured to facilitate compression or pliability of the bodies 12 when a force is applied thereto and/or may be configured to facilitate receiving a component of the closure structure 30 having a particular configuration or design. To facilitate different pliability of the implantable device 10 at different circumferential locations of the implantable device 10, different shapes of the openings 41 and/or the channels 41a may be utilized at different circumferential locations of the bodies 12.

Figure 21:
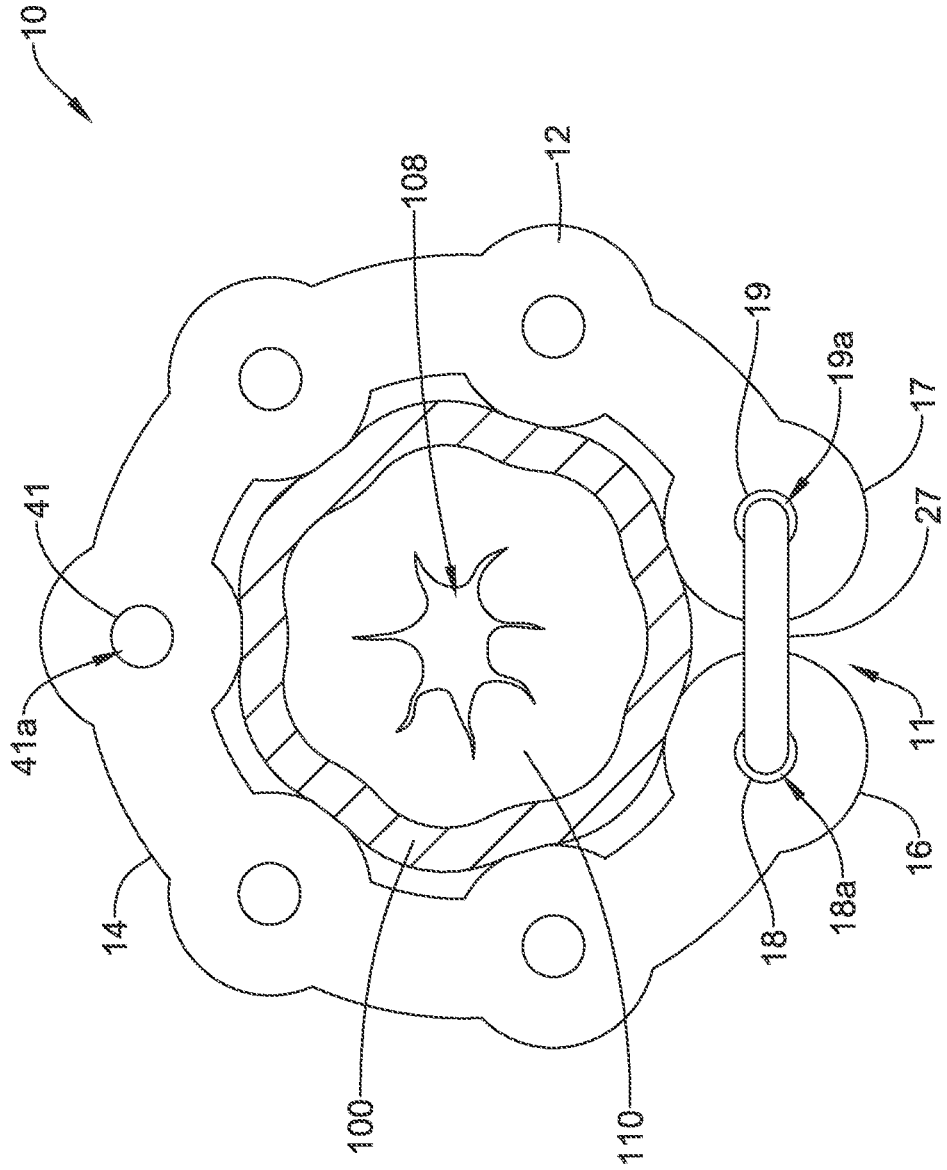
FIG. 21 is a schematic cross-section view of a tissue structure, with an illustrative implantable device implanted around the tissue structure.
Figure 22:
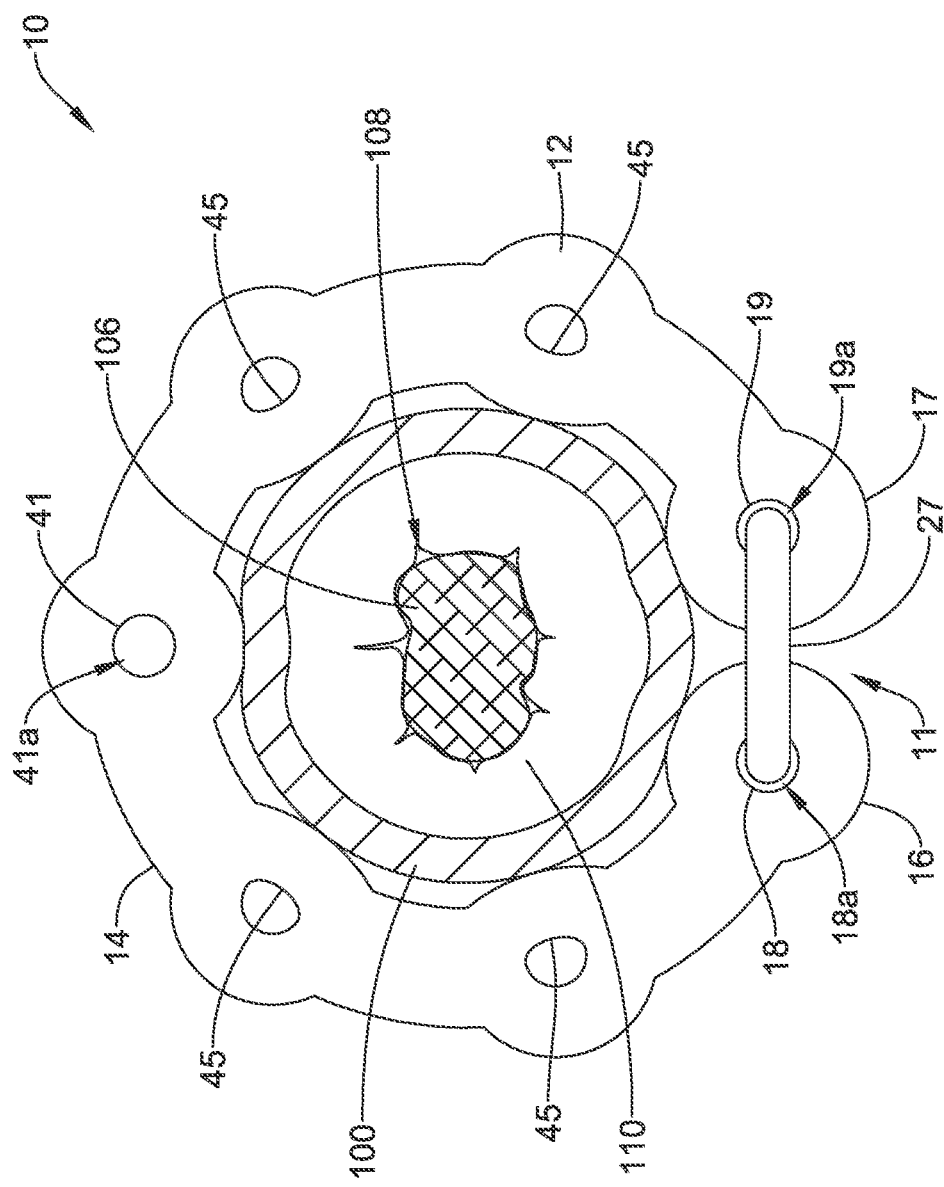
FIG. 22 is a schematic cross-section view of a tissue structure, with an illustrative implantable device implanted around the tissue structure and a bolus passing through a sphincter in the tissue structure.

FIGS. 21 and 22 schematically depict the body tissue 100 with the implantable device 10 applied thereto at a position at or adjacent to the sphincter 110, where the implantable device 10 may be applying a soft pressure to the body tissue 100 and may include the openings 41 having the channels 41a with the connector 27 extending through the first opening 18, the second opening 19, the first channel 18a, and the second channel 19a to secure the terminal ends 16, 17 of the implantable device 10 relative to one another. Similar to as shown in and discussed with respect to FIG. 3, when the implantable device 10 implanted around or adjacent to the sphincter 110, the sphincter 110 and the implantable device 10 may work together to resist expansion of the lumen 108 until a radially outward expansion force acting on the body tissue 100 from the lumen 108 reaches a threshold level due to a minimum force needed to radially adjust a portion of the implantable device 10. However, in addition to or as an alternative to an exterior circumference of the implantable device 10 expanding and/or one or more of the bodies 12 articulating or flexing, as discussed with respect to FIGS. 3-6, one or more of the bodies 12 of the implantable device 10 depicted in FIGS. 21 and 22 are configured to compress when the radially outward force acting on the implantable device 10 has reached or gone beyond the threshold level.

FIG. 22 depicts the bolus 106 (e.g., a food body or other object) passing through the lumen 108 and acting on (e.g., enlarging and/or opening) the sphincter 110. Once a threshold level of radially outward force has been reached, as is depicted in FIG. 22, the lumen 108 through the sphincter 110 may enlarge, allow the bolus 106 to pass through the sphincter 110, and cause the body tissue 100 to act on (e.g., apply a radially outward force to) the implantable device 10 extending around the body tissue 100. In response to the radially outward forces acting on the implantable device 10 reaching or exceeding the threshold level, one or more openings 41 and/or associated channels 41a may have a deflected wall 45 (e.g., the deflected wall may be a portion of the body moving radially outward). That is, the openings 41 and the associated channels 41a may be configured to absorb radially outward forces acting on the implantable device 10 by allowing the wall 45 to deflect into the channel 41a and/or otherwise deform the opening 41 and/or the channel 41a. In some cases, a shape, size, and/or other suitable property of the opening 41 and/or the associated channel 41a may be configured to establish a radially outward force threshold level (i.e., a level of radially outward force acting on the implantable device 10) at which the wall 45 of the opening 41 and/or the channel 41a may deflect and/or may be configured for one or more other suitable purposes, while allowing the implantable device 10 in a static force state to apply a soft pressure to the body tissue 100.

Figure 23:
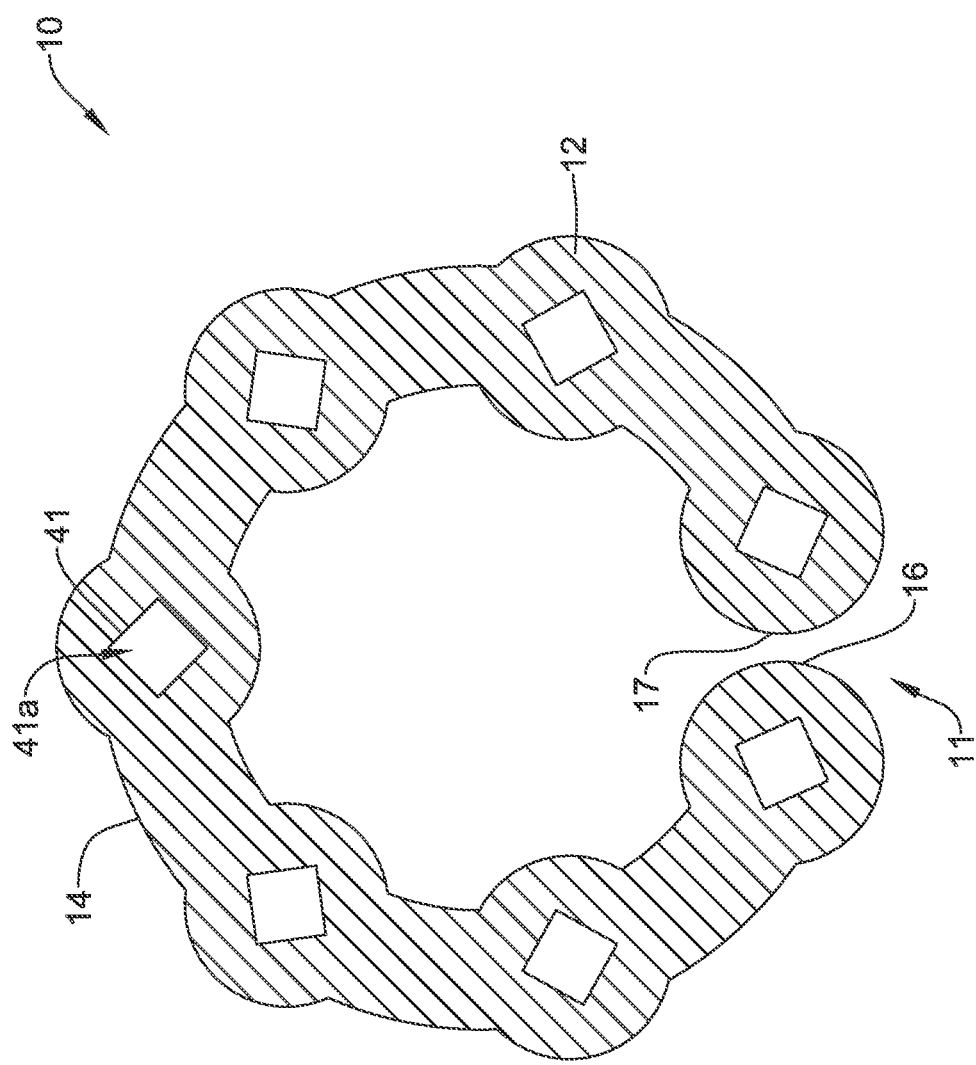
Figure 24:
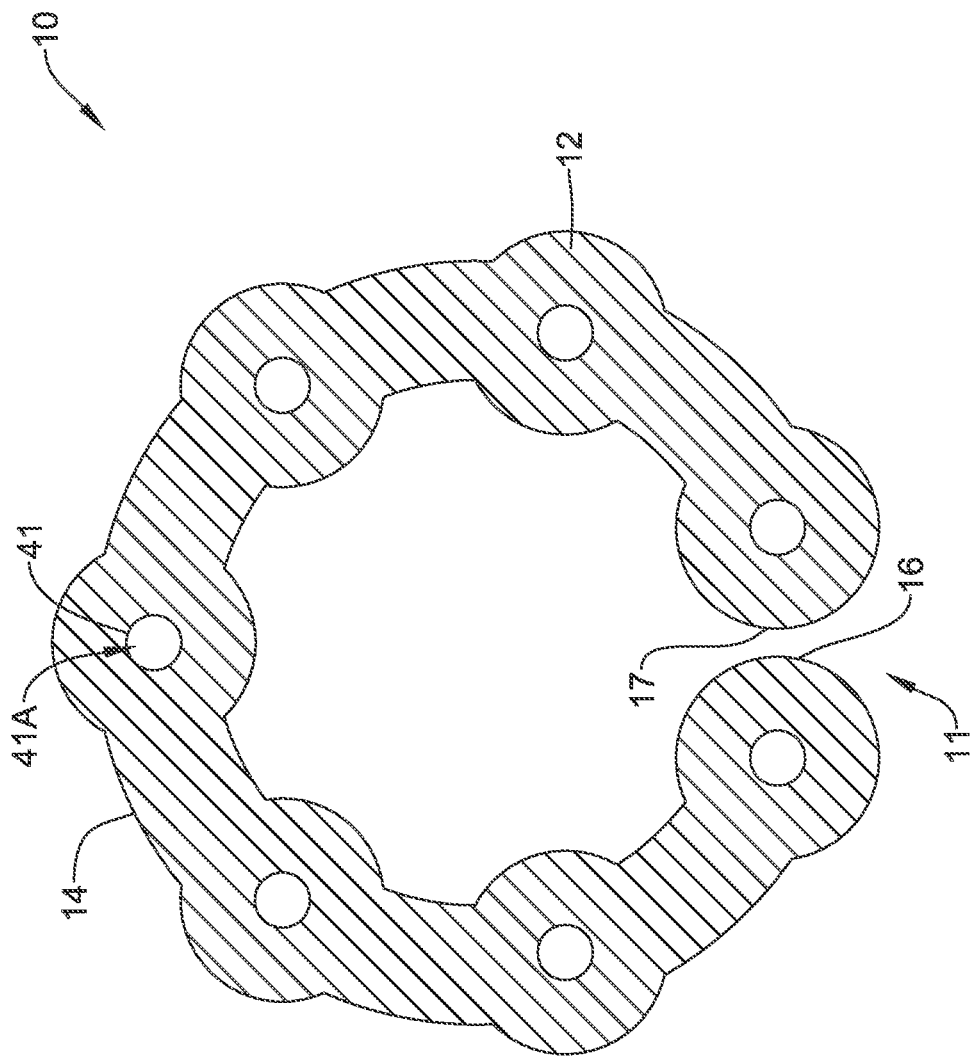
Figure 25:
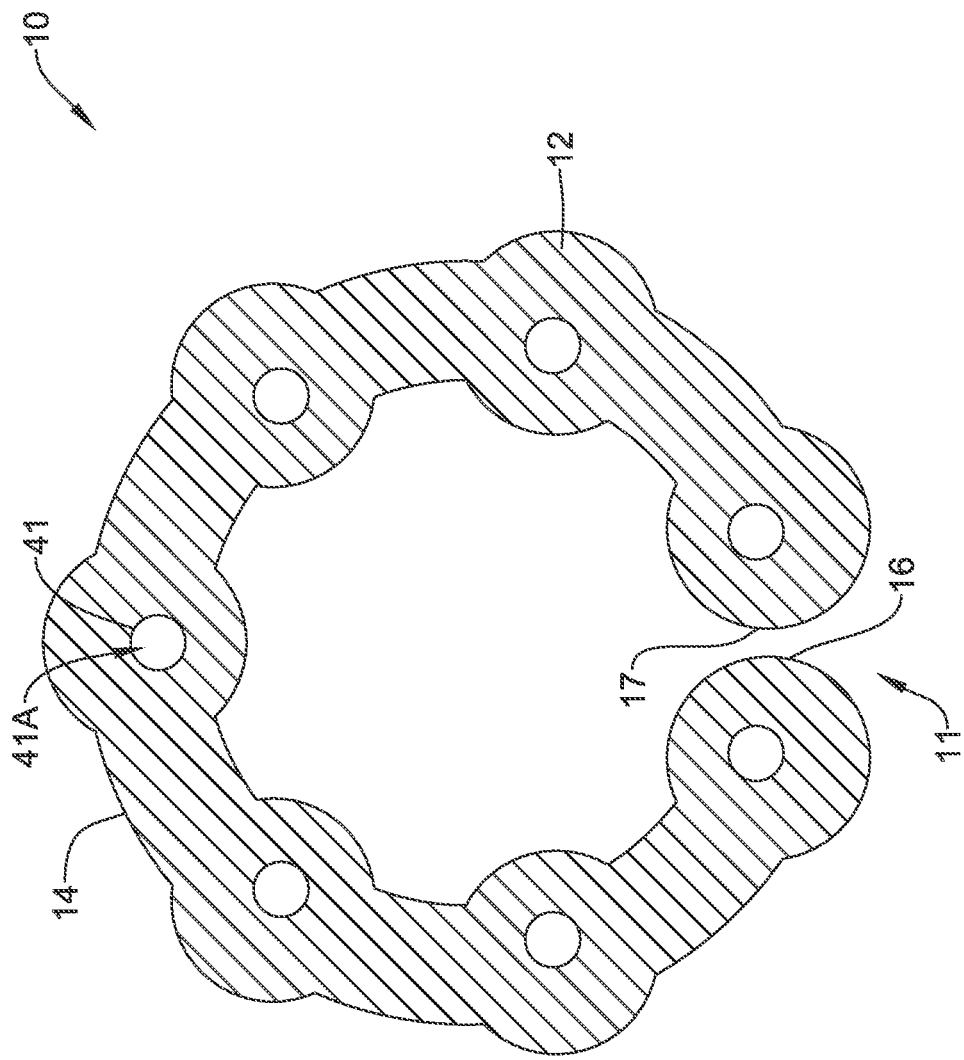
Figure 26:
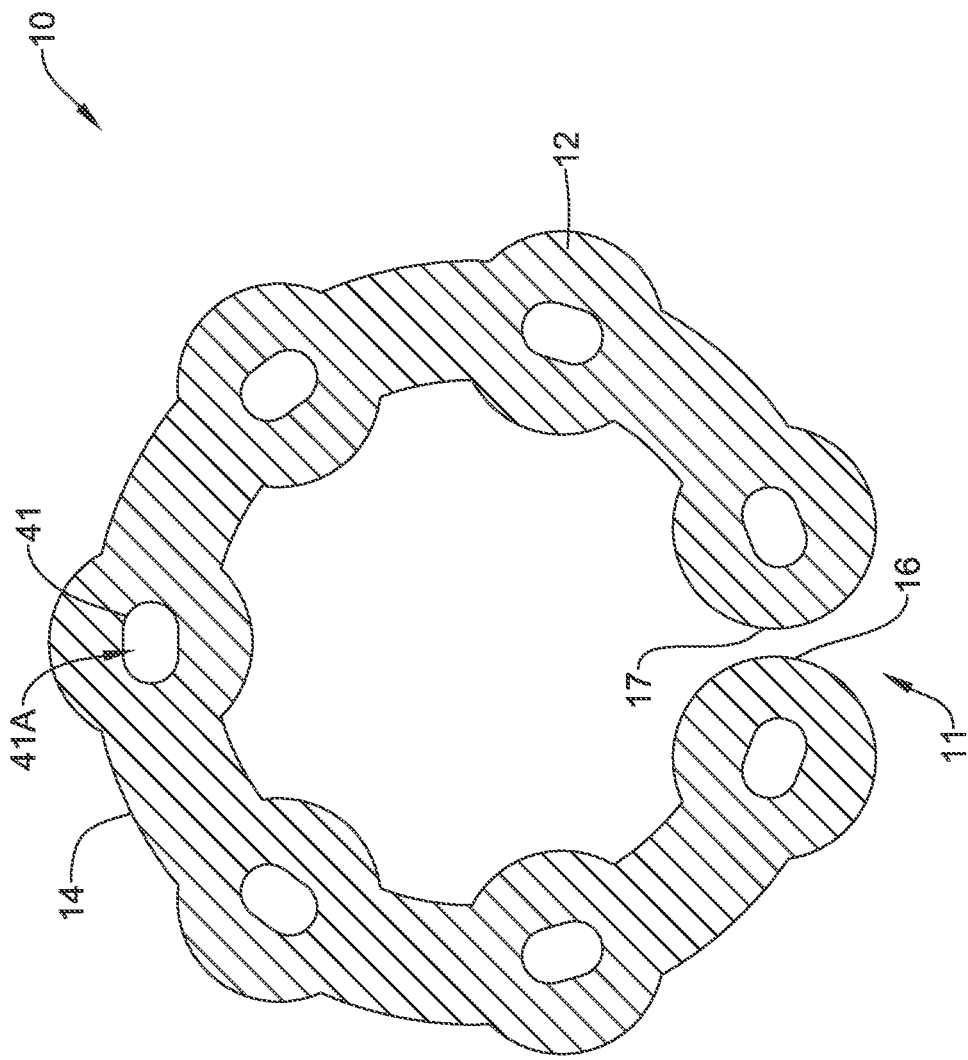

FIGS. 23-27 depict various shapes and configurations of the optional openings 41 and associated channels 41a extending at least partially into or through the bodies 12 of the implantable device 10. FIG. 23 depicts the opening 41 and the channel 41a having a rectangular or square cross-section. FIG. 24 depicts the opening 41 and the channel 41 having a centered, circular cross-section. FIG. 25 depicts the opening 41 and the channel 41 having an off-centered, circular cross-section. FIG. 26 depicts the opening 41 and the channel 41a having an oval or elongated circle cross-section. FIG. 27 depicts the opening 41 and the channel 41a having a star-shaped cross-section. Other shapes and concepts for the openings 41 and/or the channels 41a of the bodies 12 may be utilized to facilitate use of the implantable device 10 with a locking structure and for establishing a desired pliability of the bodies 12 and/or the implantable device 10.

The materials that can be used for the various components of implantable device 10 (and/or other devices disclosed herein). For simplicity purposes, the following discussion makes reference to implantable device 10. However, this is not intended to limit the devices and methods described herein.

Implantable device 10 (and/or other devices disclosed herein) and/or other components of implantable device 10 (and/or other devices disclosed herein) may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, microporous foam, bioabsorbable material, closed cell foam, open cell foam, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of implantable device 10 (and/or other devices disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids the user of implantable device 10 (and/or other devices disclosed herein) in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of implantable device 10 (and/or other devices disclosed herein) to achieve the same result.

In some embodiments, a degree of Magnetic Resonance Imaging (MRI) compatibility is imparted into implantable device 10 (and/or other devices disclosed herein). For example, implantable device 10 (and/or other devices disclosed herein), or portions thereof, may be made of a material that does not substantially distort the image and create substantial artifacts (e.g., gaps in the image). Certain ferromagnetic materials, for example, may not be suitable because they may create artifacts in an MRI image. Implantable device 10 (and/or other devices disclosed herein), or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An implantable device for implantation around a body tissue structure comprising:
    a plurality of pliable bodies, each pliable body spaced from an adjacent pliable body of the plurality of pliable bodies;
    an interconnecting region extending between two sequential pliable bodies of the plurality of pliable bodies, the plurality of pliable bodies and the interconnecting region are interconnected without a skeleton structure extending through the plurality of pliable bodies and the interconnecting region; and
    wherein the plurality of pliable bodies and the interconnecting region are configured to extend around a body tissue structure in a relaxed configuration and a portion of one or more of the plurality of pliable bodies is configured to move radially outward in a stressed configuration in response to a radially outward force acting on the one or more of the plurality of pliable bodies, and
    wherein at least one of the plurality of pliable bodies is configured to rotate independent of rotation of at least one adjacent pliable body.

2. The implantable device of claim 1, wherein each pliable body of the plurality of pliable bodies have a predetermined height dimension of or between ³⁄₁₆ inch to one (1) inch.

3. The implantable device of claim 1, wherein the plurality of pliable bodies are formed from a silicone material.

4. The implantable device of claim 1, wherein the plurality of pliable bodies and the interconnecting region connect to form a continuous structure, the implantable device further comprises:
    a closure structure configured to connect a first end of the continuous structure to a second end of the continuous structure to form a closed loop.

5. The implantable device of claim 1, wherein each pliable body of the plurality of pliable bodies are equally spaced apart from adjacent pliable bodies.

6. The implantable device of claim 1, wherein one or more pliable bodies of the plurality of pliable bodies are configured to promote growth of a scar tissue around the implantable device.

7. The implantable device of claim 1, wherein one or more of the plurality of pliable bodies includes an opening extending at least partially through the pliable body.

8. An implantable device for implantation around a body tissue structure comprising:
    a plurality of bodies arranged in a series and interconnected forming one continuous structure of a single pliable material; and
    wherein the one continuous structure is configured to be applied to an exterior surface of the body tissue structure and at least one of the plurality of bodies is configured to rotate radially outward relative to an adjacent body of the plurality of bodies in response to a radially outward force applied to the one continuous structure.

9. The implantable device of claim 8, wherein each body of the plurality of bodies has a predetermined height dimension of or between ³⁄₁₆ inch to one (1) inch.

10. The implantable device of claim 8, wherein each body of the plurality of bodies are configured to articulate so as to conform to movement of the body tissue structure.

11. An implantable device for implantation around a body tissue comprising:
    a plurality of bodies formed from a pliable material, wherein two or more bodies of the plurality of bodies are interconnected and form a continuous structure of a single material and having a first end and a second end; and
    wherein one or more of the plurality of bodies are configured to move radially outward about an axis in response to a radially outward force acting thereon when the continuous structure is implanted around a body tissue.

12. The implantable device of claim 11, wherein the pliable material includes a silicone material.

13. The implantable device of claim 11, further comprising:
    a closure structure including a first portion located at or adjacent to the first end and a second portion located at or adjacent to the second end; and
    wherein the first portion is configured to releasably engage the second portion to form a closed loop.

14. The implantable device of claim 11, further comprising:
    a closure structure including a first portion and a second portion; and
    wherein the first portion of the closure structure is configured to engage the first end of the continuous structure and the second portion of the closure structure is configured to engage the second end of the continuous structure to form a closed loop.

15. The implantable device of claim 11, wherein the one or more of the plurality of bodies has a height greater than a width.

16. The implantable device of claim 11, wherein the one or more of the plurality of bodies includes an opening extending into the body.

17. The implantable device of claim 11, wherein the one or more of the plurality of bodies includes a channel having a wall that is configured to deflect in response to the radially outward force acting thereon.

* * * * *